(12) United States Patent
Goodchild et al.

(10) Patent No.: US 8,975,245 B2
(45) Date of Patent: *Mar. 10, 2015

(54) ANAESTHETIC FORMULATION

(71) Applicant: Drawbridge Pharmaceuticals Pty Ltd, Southbank (AU)

(72) Inventors: Juliet Marguerite Goodchild, Malvern (AU); Colin Stanley Goodchild, Malvern (AU); Benjamin James Boyd, Warrandyte (AU)

(73) Assignee: Drawbridge Pharmaceuticals Pty Ltd, Southbank, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,751

(22) Filed: Nov. 1, 2013

(65) Prior Publication Data

US 2014/0066417 A1    Mar. 6, 2014

Related U.S. Application Data

(63) Continuation of application No. 13/574,201, filed as application No. PCT/AU2011/000050 on Jan. 19, 2011, now Pat. No. 8,697,678.

(60) Provisional application No. 61/297,249, filed on Jan. 21, 2010, provisional application No. 61/385,318, filed on Sep. 22, 2010.

(51) Int. Cl.
| | | |
|---|---|---|
| *A61K 31/56* | (2006.01) | |
| *A61K 47/40* | (2006.01) | |
| *A61K 31/57* | (2006.01) | |
| *A61K 47/48* | (2006.01) | |
| *B82Y 5/00* | (2011.01) | |
| *A61K 31/573* | (2006.01) | |

(52) U.S. Cl.
CPC ................. *A61K 47/40* (2013.01); *A61K 31/56* (2013.01); *A61K 31/57* (2013.01); *A61K 47/48969* (2013.01); *B82Y 5/00* (2013.01); *A61K 31/573* (2013.01)
USPC ......................................................... 514/178

(58) Field of Classification Search
CPC ...................... A61K 47/48969; A61K 31/573
See application file for complete search history.

(56) References Cited

U.S. PATENT DOCUMENTS

| | | |
|---|---|---|
| 2003/0055023 A1 | 3/2003 | Rajewski et al. |
| 2003/0073665 A1 | 4/2003 | Thompson et al. |

FOREIGN PATENT DOCUMENTS

| | | |
|---|---|---|
| EP | 0399716 B1 | 1/1994 |
| WO | WO 93/17711 A1 | 9/1993 |
| WO | WO 01/70234 A1 | 9/2001 |
| WO | WO 2004/039426 A2 | 5/2004 |

OTHER PUBLICATIONS

Brewster, M.E. et al. 1989 "Development of a Non-Surfactant Formulation for Alfaxalone Through the Use of Chemically-Modified Cyclodextrins" *Journal of Parenteral Science & Technology* 43: 262-265.
Brewster, M.E. et al. 1995 "Preparation, Characterization, and Anesthetic Properties of 2-hydroxypropyl-β-cyclodextrin Complexes of Pregnenolone in Rat and Mouse" *Journal of Pharmaceutical Sciences* 84: 1154-1159.
Chisari, M. et al. 2009 "The Influence of Neuroactive Steroid Lipophilicity on GABAA Receptor Modulation: Evidence for a Low-Affinity Interaction" *J Neurophysiol* 102: 1254-1264.
Egan, T.D. et al. 2003 "The Pharmacokinetics and Pharmacodynamics of Propofol in a Modified Cyclodextrin Formulation (Captisol®) Versus Propofol in a Lipid Formulation (Diprivan®): An Electroencephalographic and Hemodynamic Study in a Porcine Model" *Anesth Analg* 97:72-79.
Ramsay, et al. 1974 "Controlled Sedation with Alphaxalone-Alphadolone" *British Medical Journal* 2: 656-659.
Sneyd, J.R. et al. 1997 "Computer-controlled infusion of ORG 21465, a water soluble steroid i.v. anaesthetic agent, into human volunteers" *British J Anaethesia* 79: 433-439.
Supplemental European Search Report, in corresponding European Application No. EP 11 73 4245, dated Jan. 17, 2014.

*Primary Examiner* — Paul Zarek
(74) *Attorney, Agent, or Firm* — Knobbe, Martens Olson & Bear, LLP

(57) ABSTRACT

The present invention relates generally to the field of drug delivery systems for neuroactive steroid anaesthetic agents. More particularly, anaesthetic and sedative formulations are provided in the form of host/guest preparations comprising one or more neuroactive steroid anaesthetics and a cyclodextrin. Particular cyclodextrins contemplated include sulfoalkyl ether cyclodextrins and modified forms thereof.

9 Claims, 9 Drawing Sheets

ANAESTHETIC FORMULATION

This application is a continuation of U.S. application Ser. No. 13/574,201, filed Aug. 30, 2012, now U.S. Pat. No. 8,697,678, which is the U.S. national phase of International Application No. PCT/AU11/00050, filed Jan. 19, 2011, which claims priority from U.S. Provisional Patent Application No. 61/297,249, filed on 21 Jan. 2010, entitled "Anaesthetic formulation" AND U.S. Provisional Patent Application No. 61/385,318 filed on 22 Sep. 2010, entitled "Anaesthetic formulation," the entire contents of which, are incorporated herein by reference.

FIELD

The present invention relates generally to the field of drug delivery systems for neuroactive steroid anaesthetic agents. More particularly, anaesthetic and sedative compositions are provided in the form of host/guest preparations comprising one or more neuroactive steroid anaesthetics and a cyclodextrin or a modified form thereof.

BACKGROUND

Bibliographic details of references provided in the subject specification are listed at the end of the specification.

Reference to any prior art is not, and should not be taken as an acknowledgment or any form of suggestion that this prior art forms part of the common general knowledge in any country.

Drug delivery systems aim to provide the required amount of drug systemically or to a targeted site for a time and under conditions sufficient to have the desired effect. Some drug delivery systems require carrier materials to mitigate particular undesirable properties of the drugs. One such type of carrier molecule is a cyclodextrin which acts as a host for a selected guest molecule.

Cyclodextrins are cyclic oligosaccharides with hydroxyl groups on their outer surface and a void central cavity which has a lipophilic character. Cyclodextrins are capable of forming inclusion complexes with hydrophobic molecules. The stability of the resulting host/guest complex depends on how readily the guest molecule occupies the central cavity of the host.

The most common cyclodextrins are α-, β- and γ-cyclodextrins consisting of 6, 7 and 8 α-1,4-linked glucose units, respectively. Cyclodextrins have relatively low solubility in water and organic solvents and this limits their use in pharmaceutical formulations. For a description of the general chemistry of cyclodextrin, reference can be made to Fromming and Szejtlic (eds), *Cyclodextrins in Pharmacy*, Kluwer: Dordrecht, The Netherlands, 1994; Atwood, Davies, MacNicol and Vogtie (Eds), *Comprehensive Supramolecular Chemistry* Vol 4, Pergamon: Oxford UK, 1996; and Thomason, *Crit Rev Ther Drug Carrier Syst* 14:1, 1997.

Alphaxalone [Alfaxalone or 3-α-hydroxy-5-α-,pregnan-11,20-dione] is a potent neuroactive steroid anaesthetic currently used in veterinary medicine (Child et al., *British Journal of Anaesthesia* 43:2-13, 1971).

Alphaxalone was widely used around the world as an intravenous anaesthetic together with alphadolone [Althesin; Alfathesin] in human patients until 1983. Although these anaesthetics have a high therapeutic index, they were nevertheless withdrawn from clinical practice due to occasional, unpredictable yet severe anaphylactoid reactions to a polyethoxylated castor oil excipient (Cremophor EL [Registered Trademark]).

Currently, a lipid formulation of di-isopropyl phenol (propofol) is the most highly used anaesthetic agent. Propofol, however, can be contraindicated in certain at risk patients due to its lowering effect on blood pressure, the effect it has on reducing cardiac output and it can adversely affect respiratory control. In particular, propofol is formulated in a lipid emulsion which can support microbial growth if contaminated. The formulation cannot, in fact, be sterilized. There have been instances where microbially contaminated propofol formulations have resulted in patients becoming infected. One other issue with the current propofol formulation is the pain induced following or during intravenous injection. Attempts to re-formulate in a water-based preparation have led to increased injection pain. Propofol also can lead to cardiovascular and respiratory depression and has a low therapeutic index of 5, i.e. only 5 times the normal anaesthetic dose can lead to death. Furthermore, the anaesthetic is incompatible with plastic storage containers and plastic syringes which complicates syringe delivery equipment which is frequently in standard use for intravenous anaesthesia and sedation. The drug can also cause hyperlipidaemia and can induce toxicity when used in a larger dose by infusion. This is particularly problematic in the intensive care setting.

A neuroactive steroid anaesthetic has the potential for being more efficacious with fewer side effects than propofol.

There is a need, therefore, to develop a suitable formulation to enable the use of a neuroactive steroid anaesthetic agent in subjects.

SUMMARY

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method step or group of elements or integers or method steps.

The present invention provides a host/guest complex formulation comprising a neuroactive steroid anaesthetic and a cyclodextrin or modified form thereof for use in inducing anaesthesia or sedation in mammalian subjects. Generally, the neuroactive steroid anaesthetic is sparingly soluble. The host/guest complex formulation is, therefore, a drug delivery system for a neuroactive steroid anaesthetic. In an embodiment, the cyclodextrin is a modified polyanionic β-cyclodextrin and the neuroactive steroid anaesthetic is selected from alphaxalone, alphadolone, acebrochol, allopregnanolone, eltanolone(pregnanolone), ganaxolone, hydroxydione, minaxolone, Org20599, Org21465 and tetrahydrodeoxycorticosterone and a pharmacologically acceptable derivative, salt or pro-drug form thereof. However, all cyclodextrins are contemplated herein including γ and α cyclodextrins or their modified forms as well as their salts. The term "derivative" includes deuterated derivatives of the neuroactive steroid anaesthetic. Deuterated derivatives are contemplated for use as improved medicaments. One or more hydrogen atoms may be replaced by deuterium. Modified forms of cyclodextrins include methylated, hydroxyalkylated, branched, alkylated, acylated and anionic cyclodextrins. By "alkylated" includes an alkyl ether derivative as well as an alkyl ether-alkyl ether cyclodextrin. The agent "alphadolone" includes its salt, alphadolone acetate. Reference to a cyclodextrin or a modified form thereof includes its salts (e.g. a sodium salt).

Accordingly, one aspect of the present invention is directed to an anaesthetic or sedative composition comprising a neuroactive steroid anaesthetic formulated with a cyclodextrin or modified form thereof.

The anaesthetic or sedative formulation of the present invention exhibits features such as being sterilizable, causes reduced incidence of pain on injection, has a larger therapeutic index relative to propofol (including a therapeutic index greater than 5), is capable of storage in a plastic container and induces a rapid induction of anaesthesia to surgical levels with similar or more rapid awakening time than propofol or Althesin (alphaxalone and alphadolone).

Hence, another aspect of the present invention provides an anaesthetic or sedative composition comprising a neuroactive steroid anaesthetic and a cyclodextrin or modified form thereof wherein the anaesthetic and cyclodextrin are formulated to provide an anaesthetic composition which exhibits a property selected from being sterilizable, exhibiting minimal pain on intravenous injection, having a therapeutic index greater than 5 and is storable in a plastic container. In an embodiment, the formulation has one, two, three or all four of these properties.

In a related embodiment, the present invention provides an anaesthetic or sedative delivery host/guest composition comprising a cyclodextrin host or a modified form thereof with a neuroactive steroid anaesthetic drug guest, the host/guest composition formulated to be sterilizable, administrable by intravenous injection with minimal pain and to exhibit a therapeutic index of greater than 5. The formulation may also be storable in a plastic container.

More particularly, the present invention provides an anaesthetic or sedative composition comprising a neuroactive steroid anaesthetic selected from alphaxalone, alphadolone, acebrochol, allopregnanolone, eltanolone (pregnanolone), ganaxolone, hydroxydione, minaxolone, Org20599, Org21465 and tetrahydrodeoxycorticosterone and pharmacologically acceptable derivatives, salts and pro-drug forms thereof formulated with a cyclodextrin or modified form thereof.

Even more particularly, the present invention is directed to an anaesthetic or sedative composition comprising a neuroactive steroid anaesthetic selected from alphaxalone, alphadolone, acebrochol, allopregnanolone, eltanolone (pregnanolone), ganaxolone, hydroxydione, minaxolone, Org20599, Org21465 and tetrahydrodeoxycorticosterone and pharmacologically acceptable derivatives, salts and pro-drug forms thereof formulated with a cyclodextrin or a modified form thereof wherein the composition exhibits a property selected from being sterilizable, exhibiting minimal pain on intravenous injection, having a therapeutic index greater than 5 and is storable in a plastic container.

A particular cyclodextrin useful in the practice of the present invention is a sulfoalkyl ether cyclodextrin such as (7) sulfobutyl ether β-cyclodextrin. This compound can be prepared as described in U.S. Pat. No. 5,376,645. Another useful cyclodextrin is an alkyl ether derivative including a sulfoalkyl ether-alkyl ether cyclodextrin. However, the present invention extends to other cyclodextrin derivatives such as methylated, hydroxyalkylated, branched, acylated and anionic forms. The anaesthetic formulation of the present invention enables injectable administration to mammalian subjects and in particular human patients.

Another aspect of the present invention provides an anaesthetic or sedative composition comprising a neuroactive steroid selected from alphaxalone, alphadolone, acebrochol, allopregnanolone, eltanolone (pregnanolone), ganaxolone, hydroxydione, minaxolone, Org20599, Org21465 and tetrahydrodeoxycorticosterone and a pharmacologically acceptable derivative, salt or pro-drug form thereof formulated with a sulfoalkyl ether cyclodextrin or modified form thereof to generate a sterilizable composition with a therapeutic index of greater than 5.

In an embodiment, the composition is also storable in a plastic container.

The formulation may comprise a buffer to maintain pH within a range of from about pH5.5 to pH8. Alternatively, the formulation may not be buffered wherein the pH of the formulation may be from about pH3 to about pH9.5. The formulation may also comprise a preservative, anti-microbial agent and/or an agent which reduces toxicity. In addition, to improve solubility and/or stability, a co-polymer may be included. Examples of suitable co-polymers include hydroxyl propyl methyl cellulose (HPMC), polyvinyl pyrollidone (PVP), and carboxymethyl cellulose (CMC).

The present invention further contemplates inducing or maintaining by infusion or intermittent bolus administration, anaesthesia or sedation in a subject, the method comprising administering an anaesthetic-effective amount of a neuroactive steroid anaesthetic formulated with a cyclodextrin, for a time and under conditions to induce anaesthesia or sedation.

More particularly, the present invention provides a method of inducing or maintaining by infusion or intermittent bolus administration, anaesthesia or sedation in a subject, the method comprising administering an anaesthetic-effective amount of a neuroactive steroid anaesthetic selected from alphaxalone, alphadolone, acebrochol, allopregnanolone, eltanolone (pregnanolone), ganaxolone, hydroxydione, minaxolone, Org20599, Org21465 and tetrahydrodeoxycorticosterone and pharmacologically acceptable derivatives, salts or pro-drug forms thereof formulated with a cyclodextrin or modified form thereof for a time and under conditions sufficient to induce anaesthesia or sedation wherein the anaesthetic or sedative formulation exhibits a property selected from being sterilizable, exhibiting minimal pain on intravenous injection and having a therapeutic index greater than 5.

In an embodiment, the formulation is also storable in a plastic container.

Generally, the molar ratio of neuroactive steroid anaesthetic to cyclodextrin is from about 1:1 to about 1:6, more particularly about 1:1 to about 1:4, even more particularly about 1:1 to 1:3 and still more particularly about 1:2.

These aspects of the present invention extend to inducing or maintaining by infusion or intermittent bolus administration, anaesthesia or sedation or both in subjects.

The formulation may be packaged for sale with a set of instructions. The instructions may include a patient management protocol comprising administering to the patient an effective amount of neuroactive steroid anaesthetic such as selected from alphaxalone, alphadolone, acebrochol, allopregnanolone, eltanolone (pregnanolone), ganaxolone, hydroxydione, minaxolone, Org20599, Org21465 and tetrahydrodeoxycorticosterone and pharmacologically acceptable derivatives, salts and pro-drug forms thereof formulated with a cyclodextrin for a time and under conditions sufficient to induce anaesthesia. As indicated above, a suitable cyclodextrin includes a sulfoalkyl ether dextrin, such as (7) sulfobutyl ether β-cyclodextrin as well as alkyl ether derivatives such as sulfoalkyl-alkyl ether cyclodextrins. Other derivatives include methylated, hydroxyalkylated, branched, alkylated, acylated and anionic cyclodextrins.

The present invention further contemplates the use of a neuroactive steroid anaesthetic and a cyclodextrin or modified form thereof, in the manufacture of a medicament to induce anaesthesia in a subject. In a particular embodiment, the neuroactive steroid anaesthetic is selected from alphaxalone, alphadolone, acebrochol, allopregnanolone, eltanolone (pregnanolone), ganaxolone, hydroxydione, minaxolone, Org20599, Org21465 and tetrahydrodeoxycorticosterone and pharmacologically acceptable derivatives, salts and pro-drug forms thereof.

Kits comprising in compartmental form a neuroactive steroid anaesthetic in a first compartment and a cyclodextrin, such as a sulfoalkyl ether cyclodextrin, in a second compartment and optionally excipients and/or co-polymers in a third or other compartment are also contemplated herein. The kit may be in the form of a modified syringe.

Labeled forms of the neuroactive steroid anaesthetic are also useful in monitoring and tracking the anaesthetic during sedation or anaesthesia. Kits and apparatus are therefore provided herein to assist in the monitoring of labelled neuroactive steroid anaesthetics. Labeled derivatives include deuterated, tritiated and other labeled agents.

Figure 1A:
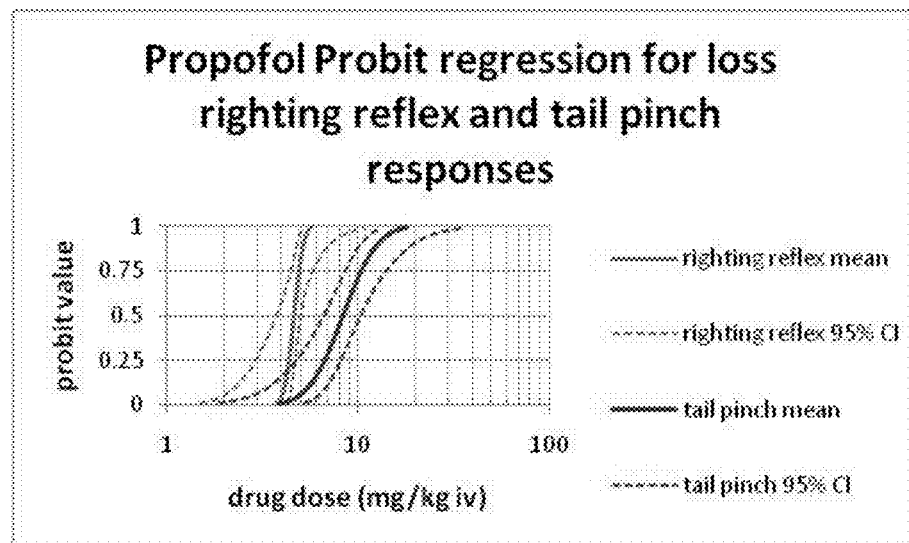
FIGS. 1a through 1f are graphical representations of experiments on male Wistar rats implanted with indwelling internal jugular vein intravenous catheters under halothane anaesthesia and then provided with propofol (a,b), Althesin [alphaxalone and alphadolone acetate] (c,d) or Phaxan$_{CD}$ [alphaxalone in a 1:2 molar complexation ratio with (7) sulfobutyl ether β-cyclodextrin] (e,f).
Figure 1B:
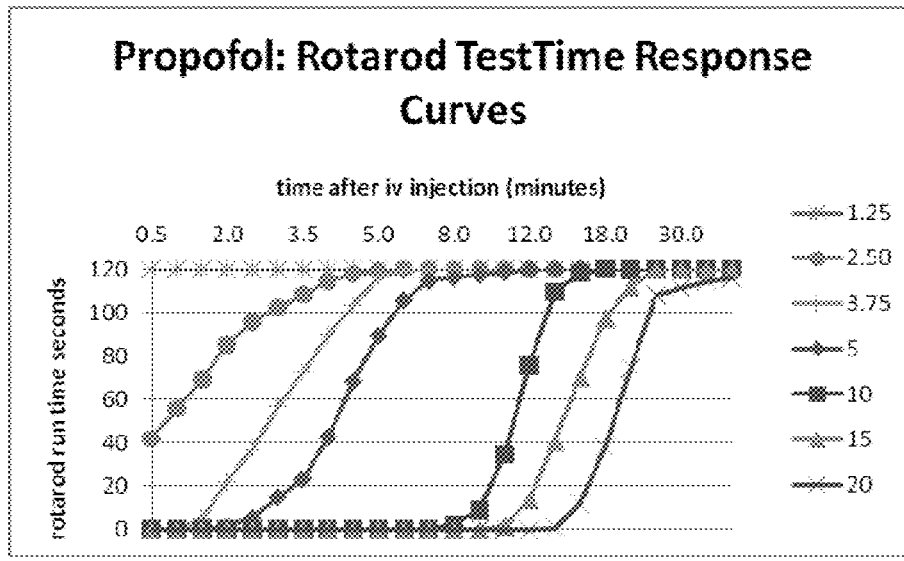
Figure 1C:
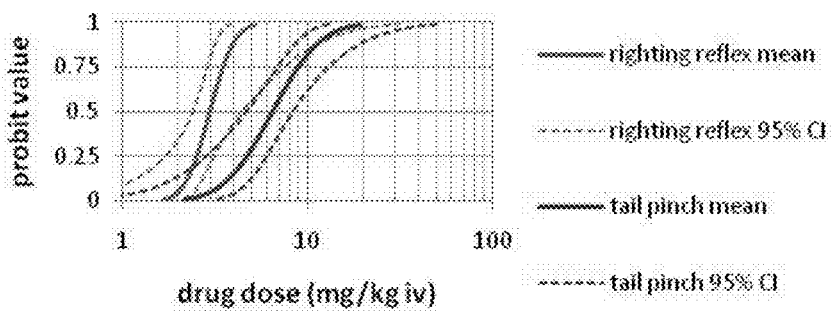
Figure 1D:
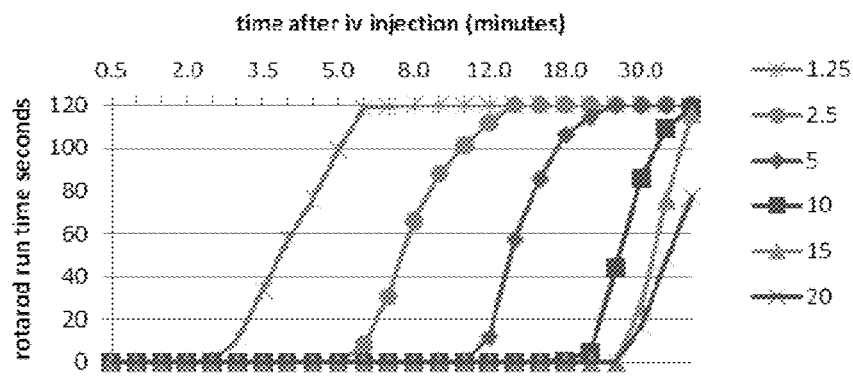
Figure 1E:
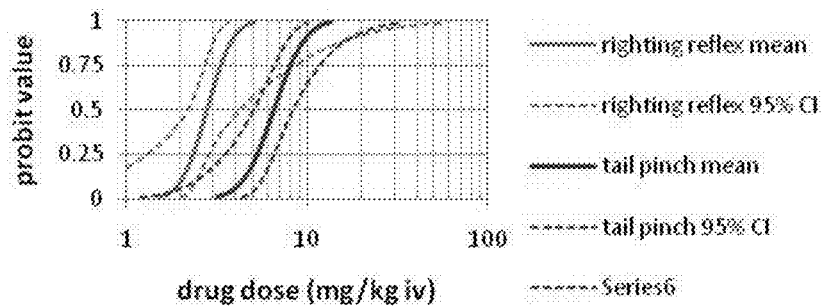
Figure 1F:
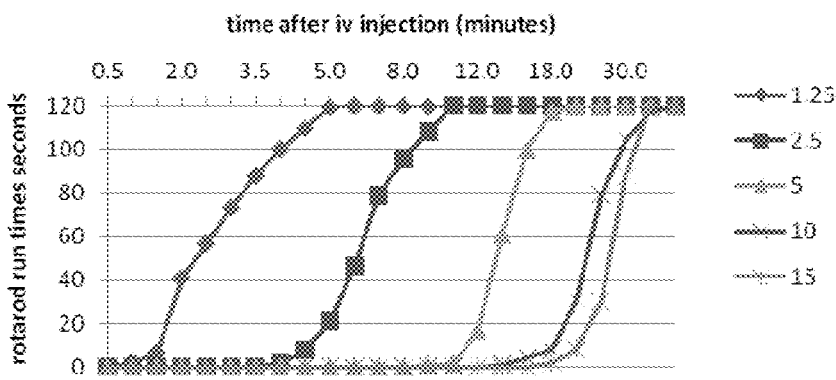

Reference to "Phaxan$_{CD}$" means an alphaxalone preparation with (7) sulfobutyl ether β-cyclodextrin.

DETAILED DESCRIPTION

The present invention provides a drug delivery system for a neuroactive steroid anaesthetic. Generally, the neuroactive steroid anaesthetic is sparingly soluble in water. The drug delivery system comprises a host carrier in the form of a cyclodextrin or modified form thereof. Reference to "cyclodextrin" includes in one embodiment an α-, β- or γ-cyclodextrin or a modified or derivatized form thereof. Reference to "cyclodextrin" in another embodiment includes a sulfoalkyl ether dextrin such as (7) sulfobutyl ether β-cyclodextrin or an alkyl ether derivative thereof such as a sulfobutyl ether-alkyl ether cyclodextrin. Derivatives of cyclodextrins include methylated, hydroxyalkylated, branched, alkylated, acylated and anionic cyclodextrins. By "alkylated" includes an alkyl ether derivative such as an alkyl ether-alkyl ether cyclodextrin. Particular cyclodextrins contemplated herein are shown in Table 7 [Uekama et al., Chem. Rev. 98: 2045-2076, 1998] and include β-cyclodextrin sulfobutyl ethers, ethyl ethers, β-cyclodextrin sulfobutyl ethers (flat), γ-cyclodextrin sulfobutyl ethers and α-cyclodextrin sulfobutyl ethers and their salts (e.g. sodium salts).

The drug delivery system of the present invention enables a neuroactive steroid anaesthetic to be administered to a subject in a sterilized form. Furthermore, the delivery itself is with less pain compared to the intravenous administration of propofol. The formulation of the present invention additionally has a therapeutic index greater than 5 (meaning that administration of greater than 5 times the anaesthetic dose can lead to death in a test animal). By "greater than 5" means a therapeutic index of between 5 and 200 including 10, 20, 30, 40, 50, 60, 70, 80, 90, 100, 110, 120, 130, 140, 150, 160, 170, 180, 190 and 200 as well as integers or fractions in between. The formulation of the present invention is also storable in a plastic container and is compatible for use in plastic delivery apparatus.

Accordingly, an aspect of the present invention provides an anaesthetic or sedative delivery host/guest composition comprising a cyclodextrin host or modified form thereof with a neuroactive steroid anaesthetic drug guest, the host/guest composition formulated to be sterilizable, administrable by intravenous injection with minimal pain and to exhibit a therapeutic index of greater than 5. In an embodiment, the formulation may also be storable in a plastic container. The formulation may exhibit one, two, three or all four of these properties.

By "reduced pain" means compared to a formulation comprising propofol as a reference.

The formulation is useful for inducing anaesthesia or sedation in mammalian subjects and in particular human subjects.

In an embodiment, the neuroactive steroid is selected from alphaxalone, alphadolone, acebrochol, allopregnanolone, eltanolone (pregnanolone), ganaxolone, hydroxydione, minaxolone, Org 20599, Org 21465 and tetrahydrodeoxycorticosterone and a pharmacologically acceptable derivative, salt or pro-drug form thereof.

An example of a pharmacologically acceptable salt is alphadolone acetate, which is encompassed by the present invention. An example of a derivative of a neuroactive steroid anaesthetic is a deuterated derivative. A "modified" cyclodextrin includes a derivative of a cyclodextrin.

Accordingly, another aspect of the present invention is directed to a drug delivery host/guest composition comprising a cyclodextrin host or modified form thereof with a neuroactive steroid anaesthetic drug guest selected from alphaxalone, alphadolone, acebrochol, allopregnanolone, eltanolone (pregnanolone), ganaxolone, hydroxydione, minaxolone, Org 20599, Org 21465 and tetrahydrodeoxycorticosterone and a pharmacologically acceptable derivative, salt or pro-drug form thereof, the host/guest composition being sterilizable, administrable by intravenous injection with minimal pain, exhibiting a therapeutic index of greater than 5 and/or storable in a plastic container. The formulation can also initiate rapid induction of anaesthesia to surgical levels with similar or more rapid wakening time compared to propofol. As indicated above, the formulation may exhibit one, two, three or all of these properties.

The composition of the present invention may be referred to as a formulation, host/guest composition, drug delivery system, medicament, anaesthetic or sedative as well as more descriptively such as an anaesthetic formulation or sedative formulation.

Another aspect of the present invention provides an anaesthetic or sedative formulation comprising a neuroactive steroid anaesthetic and a cyclodextrin or modified form thereof, the formulation exhibiting properties including being sterilizable, inducing reduced pain on intravenous administration, having a therapeutic index of greater than 5 and/or being storable in a plastic container.

More particularly, the present invention relates to an anaesthetic or sedative formulation comprising a neuroactive steroid anaesthetic selected from alphaxalone, alphadolone, acebrochol, allopregnanolone, eltanolone (pregnanolone), ganaxolone, hydroxydione, minaxolone, Org 20599, Org 21465 and tetrahydrodeoxycorticosterone and a pharmacologically acceptable derivative, salt or pro-drug form thereof, the formulation exhibiting properties including being sterilizable, inducing reduced pain on intravenous administration and having a therapeutic index of greater than 5.

In an embodiment, the formulation is also storable in a plastic container.

The present invention extends to mixtures of two or more neuroactive steroid anaesthetic drugs such as a composition comprising alphaxalone and alphadolone and/or alphadolone acetate or their pharmacologically acceptable derivatives, salts or pro-drug forms.

A "pharmacologically acceptable derivative" is a derivative that still induces anaesthesia whilst not increasing adverse side effects. The term "derivative" includes deuterated derivatives where one or more hydrogen atoms are replaced with deuterium. This can lead to improved efficacy. Furthermore, the anaesthetic agents may be subject to alkylation, alkoxylation, acetylation and/or phosphorylation to generate other derivatives. Other types of derivatives include deuterated or tritiated or other labeled forms useful for monitoring and tracking the anaesthetic in the body. The terms "derivative" and "modified form" are used interchangeably herein. Salts of alphadolone include alphadolone acetate. Reference to pro-drugs include transported pro-drugs.

In an embodiment, the cyclodextrin is a β-cyclodextrin or a modified form thereof such as but not limited to a sulfoalkyl ether dextrin. A particularly useful sulfoalkyl ether dextrin is (7) sulfobutyl ether β-cyclodextrin. Alkyl ether derivatives are also contemplated such as a sulfoalkyl ether-alkyl ether cyclodextrin. An example of an alkyl ether derivative is a sulfobutyl ether-alkyl ether cyclodextrin. Other cyclodextrins contemplated herein are listed in Table 7 and include methylated, hydroxyalkylated, alkylated, branched, acylated and anionic derivatives.

Accordingly, an aspect of the present invention provides an anaesthetic or sedative delivery host/guest composition comprising a sulfoalkyl ether dextrin host or modified form thereof with a neuroactive steroid anaesthetic drug guest, the host/guest composition formulated to be sterilizable, administrable by intravenous injection with minimal pain, exhibiting a therapeutic index of greater than 5. In an embodiment, the formulation may also be storable in a plastic container.

Another aspect of the present invention is directed to a drug delivery host/guest composition comprising a sulfoalkyl ether dextrin host or modified form thereof with a neuroactive steroid anaesthetic drug guest selected from alphaxalone, alphadolone, acebrochol, allopregnanolone, eltanolone (pregnanolone), ganaxolone, hydroxydione, minaxolone, Org 20599, Org 21465 and tetrahydrodeoxycorticosterone and a pharmacologically acceptable derivative, salt or pro-drug form thereof, the host/guest composition to be sterilizable, administrable by intravenous injection with minimal pain and exhibiting a therapeutic index of greater than 5.

In an embodiment, the composition is also storable in a plastic container.

Another aspect of the present invention provides an anaesthetic or sedative formulation comprising a neuroactive steroid anaesthetic and a sulfoalkyl ether dextrin or modified form thereof, the formulation exhibiting properties including being sterilizable, inducing reduced pain on intravenous administration, having a therapeutic index of greater than 5 and/or being storable in a plastic container.

As indicated above one particularly useful sulfoalkyl ether dextrin is (7) sulfobutyl ether β-cyclodextrin. Of the properties exhibited, in a particular embodiment, the formulation exhibits two or more, three or more or all properties. These properties include imitating rapid induction of anaesthesia to surgical levels with similar or more rapid wakening time such as compared to propofol.

The formulation between the neuroactive steroid and cyclodextrin is generally in a molar ratio of from 1:1 to 1:6 (neuroactive steroid:cyclodextrin), more particularly about 1:1 to 1:4, even more particularly about 1:1 to 1:3 and still more particularly about 1:2. The range 1:1 to 1:6 includes 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3; 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9 and 1:6.

Accordingly, the present invention provides a drug delivery host/guest composition comprising a cyclodextrin host or modified form thereof with a neuroactive steroid drug guest, wherein the molar ratio of neuroactive steroid to cyclodextrin is from about 1:1 to about 1:6 and wherein the composition is formulated to be sterilizable, administrable by intravenous injection with minimal pain and exhibiting a therapeutic index of greater than 5. In an embodiment, the formulation may also be storable in a plastic container.

More particularly, the present invention is directed to a drug delivery host/guest composition comprising a cyclodextrin selected from an α-, β- or γ-cyclodextrin or a modified form thereof including a sulfoalkyl ether dextrin or sulfoalkyl ether-alkyl ether derivative or other derivatives listed in Table 7 and a neuroactive steroid drug guest selected from alphaxalone, alphadolone, acebrochol, allopregnanolone, eltanolone (pregnanolone), ganaxolone, hydroxydione, minaxolone, Org 20599, Org 21465 and tetrahydrodeoxycorticosterone and a pharmacologically acceptable derivative, salt or pro-drug form thereof, wherein the molar ratio of a neuroactive steroid to cyclodextrin is from about 1:1 to about 1:6 and wherein the composition is formulated to be sterilizable, administrable by intravenous injection with minimal pain and to exhibit a therapeutic index of greater than 5. In one embodiment, the (7) sulfobutyl ether β-cyclodextrin comprises less than 100 ppm of a phosphate and has an absorption of less than 0.5 AU due to a drug-degrading enzyme, as determined by UV/v is spectrophotometry at a wave length of 245 nm to 270 nm for an aqueous solution containing 300 mg of the dextrin per ml of solution in a cell having a 1 cm path length. In an embodiment, the formulation may also be storable in a plastic container.

The anaesthetic composition of the present invention may in one embodiment comprise a buffer such as a phosphate or tris or citrate phosphate buffer to maintain the pH from about 5.5 to about pH8. This includes pH values of 5.5, 6, 6.5, 7, 7.5 and 8. Alternatively, the composition does not comprise a buffer and the pH being from about pH3 to about pH 9.5 such as pH3, 3.5, 4, 4.5, 5, 5.5, 6, 6.5, 7, 7.5, 8, 8.5, 9 or 9.5.

In a further aspect, the formulations of the present invention also include one or more agents such as excipients and/or preservatives, microbial retardants. Other agents may also be included to reduce toxicity. Agents include, for example, EDTA, benzyl alcohol, bisulphites, monoglyceryl ester of lauric acid (Monolaurin), capric acid and/or its soluble alkaline salts or its monoglyceryl ester (Monocaprin), edetate, and capric acid and/or its soluble alkaline salts or its monoglyceryl ester (Monocaprin) and edetate. The formulation may also contain one or more co-polymers to assist in solubility or stability of the anaesthetic agent. Examples include hydroxy propyl methyl cellulose (HPMC), polyvinyl pyrollidone (PVP) and/or carboxymethyl cellulose (CMC).

Conveniently, the neuroactive steroid anaesthetic is provided at a concentration of from about 0.5 to 100 mg/ml in a saline suspension comprising the cyclodextrin. Such a concentration includes 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 mg/ml of drug. As indicated above, the composition is generally formulated so that the molar ratio of neuroactive steroid to cyclodextrin is from about 1:1 to about 1:6, particularly from about 1:1 to 1:4, even more particularly from about 1:1 to 1:3 and most particularly about 1:2.

Reference to any particular neuroactive steroid or their salts includes a racemic mixture of enantiomers of each anaesthetic as well as a single enantiomer of the agent.

In a particular embodiment, the neuroactive steroid is alphaxalone, alphadolone and/or alphadolone acetate. In one embodiment, alphaxalone is in the formulation at a concentration of from 1 to 100 mg/ml such as 10 mg/ml. In another embodiment, alphadolone or alphadolone acetate is present at 0.5 to 50 mg/ml such as 3 mg/ml.

The formulations herein are for in vivo delivery meaning that the neuroactive steroid anaesthetic is delivered by intravenous, sub-cutaneous, intraperitoneal, intrathecal, intramuscular, intravitreal, transdermal, suppository (rectal), pessary (vaginal), inhalation, intranasal and the like. Most effectively, the formulation is an intravenous (iv) formulation.

Accordingly, another aspect of the present invention provides an injectable formulation of a neuroactive steroid anaesthetic selected to be sterilizable, administrable by intravenous injection with minimal pain, exhibiting a therapeutic index of greater than 5 and storable in a plastic container formulated with cyclodextrin, such as (7) sulfobutyl ether β-cyclodextrin or an alkyl ether derivative.

The neuroactive steroid anaesthetic may be used alone or in combination with another anaesthetic or sedative or other active agent. In one embodiment, alphaxalone is used with alphadolone or its salt, alphadolone acetate. Hence, reference to "alphadolone" includes alphadolone acetate. The composition may comprise, therefore alphaxalone or alphadolone alone or a combination of alphaxalone and alphadolone or any of their derivatives, salts or pro-drug forms.

Hence, in a particular embodiment, the present invention further provides a composition comprising alphaxalone or a pharmacologically acceptable derivative, salt or pro-drug thereof and/or alphadolone or a pharmacologically acceptable derivative, salt or pro-drug thereof formulated with a sulfoalkyl ether dextrin, such as (7) sulfobutyl ether β-cyclodextrin wherein the molar ratio of alphaxalone and/or alphadolone to dextrin is from about 1:1 to about 1:6. Reference can conveniently be made to Remington's Pharmaceutical Sciences, Mack Publishing Company, Eaton, USA, 1990 and Rowe's Handbook of Pharmaceutical Excipients, 2009 for formulation methods and reagents.

The present invention contemplates inducing or maintaining by infusion or intermittent bolus administration, anaesthesia in a human subject, the method comprising administering an anaesthetic-effective amount of a neuroactive steroid anaesthetic formulated with a cyclodextrin, such as sulfoalkyl ether dextrin, for a time and under conditions to induce anaesthesia.

More particularly, the present invention provides a method of inducing or maintaining by infusion or intermittent bolus administration, anaesthesia in a human subject, the method comprising administering an anaesthetic-effective amount of a neuroactive steroid anaesthetic selected from alphaxalone, alphadolone, acebrochol, allopregnanolone, eltanolone (pregnanolone), ganaxolone, hydroxydione, minaxolone, Org20599, Org21465 and tetrahydrodeoxycorticosterone and a pharmacologically acceptable derivative, salt or pro-drug form thereof formulated with a cyclodextrin, such as (7) sulfobutyl ether β-cyclodextrin, for a time and under conditions sufficient to induce anaesthesia, wherein the anaesthetic formulation is sterilizable, administrateable by intravenous injection with minimal pain and exhibits a therapeutic index of greater than 5. Additionally, the formulation can initiate rapid anaesthesia with similar or more rapid wakening time compared with propofol or Althesin (Registered Trademark). The formulation may also be storable in a plastic container.

The present invention extends to inducing or maintaining by infusion or intermittent bolus administration, sedation. Hence, another aspect of the present invention provides a method of inducing or maintaining by infusion or intermittent bolus administration, sedation in a subject, the method comprising administering a sedation-effective amount of a neuroactive steroid anaesthetic formulated with a cyclodextrin such as sulfoalkyl ether dextrin, for example, (7) sulfobutyl ether β-cyclodextrin, for a time and under conditions sufficient to induce sedation.

Reference to "(7) sulfobutyl ether β-cyclodextrin" includes methylated, hydroxyalkylated, branched, alkylated, acylated and anionic derivatives thereof such as a sulfobutyl ether-alkyl ether β-cyclodextrin. Other derives include β-cyclodextrin sulfobutyl ethers, ethyl ethers, β-cyclodextrin sulfobutyl ethers (flat), γ-cyclodextrin sulfobutyl ethers and α-cyclodextrin sulfobutyl ethers and their salts (e.g. sodium salts).

As indicated above, a particular subject is a human subject.

The anaesthetic formulation may be packaged for sale with instructions for use. The use includes a patient management protocol comprising administering to the patient an effective amount of neuroactive steroid anaesthetic such as selected from alphaxalone, alphadolone and pharmacologically acceptable derivatives, salts and pro-drug forms thereof formulated with a cyclodextrin such as a sulfoalkyl ether dextrin, for example, (7) sulfobutyl ether β-cyclodextrin, for a time and under conditions sufficient to induce anaesthesia.

The present invention further contemplates the use of a neuroactive steroid anaesthetic and a cyclodextrin, such as a sulfoalkyl ether dextrin, for example, (7) sulfobutyl ether β-cyclodextrin, in the manufacture of a medicament to induce anaesthesia in a subject such as a human subject. In a particular embodiment, the neuroactive steroid anaesthetic is selected from alphaxalone, alphadolone and pharmacologically acceptable derivatives, salts and pro-drug forms thereof. In another embodiment, the anaesthetic is selected from acebrochol, allopregnanolone, eltanolone (pregnanolone), ganaxolone, hydroxydione, minaxolone, Org20599, Org21465 and tetrahydrodeoxycorticosterone and a pharmacologically acceptable derivative, salt or pro-drug form thereof.

In terms of an anaesthetic-effective amount, this is generally around 0.25 mg/kg to about 100 mg/kg body weight. A sedative-effective amount is provided in similar or lower amounts and includes from about 0.05 mg/kg to about 10 mg/kg body weight.

The present invention further provides a kit. The kit may be in any form including a syringe or modified syringe. A kit may comprise alphaxalone and/or alphadolone or other neuroactive steroid anaesthetic or their derivatives, salts or pro-drug forms in one or more compartments and a sulfoalkyl ether dextrin in a further compartment as well as excipients in subsequent compartments. The contents of the compartments may be admixed prior to use.

In a particular embodiment, the present invention provides a formulation comprising alphaxalone and/or alphadolone and/or pharmacologically acceptable derivatives, salts or pro-drug forms thereof complexed with the sulfobutyl ether cyclodextrin, for use in inducing or maintaining by infusion or intermittent bolus administration, anaesthesia or sedation in human subject.

The anaesthetic forms may be labeled such as deuterated or tritiated forms or by other labels to facilitate monitoring and tracking of the anaesthetics in the body. Kits and apparatus are provided, therefore, to monitor labeled neuroactive steroid anaesthetics.

Whilst the present invention is particularly directed to anaesthetic formulations for use in humans, the formulations may also be used in animals such as for clinical trials or veterinary use. Non-human animals contemplated herein include rats, mice, guinea pigs, hamsters, sheep, pigs, dogs, cats, horses, cows, goats, camels and non-human primates.

Hence, the present invention provides an anaesthetic or sedative composition comprising a neuroactive steroid anaesthetic and a cyclodextrin or modified form thereof wherein the composition has the following properties:
(i) the neuroactive steroid and cyclodextrin are formulated in a molar ratio of from about 1:1 to about 1:6;
(ii) the neuroactive steroid is selected from alphaxalone, alphadolone, acebrochol, allopregnanolone, eltanolone (pregnanolone), ganaxolone, hydroxydione, minaxolone, Org20599, Org21465 and tetrahydrodeoxycorticosterone and a pharmacologically acceptable derivative, salt or pro-drug form thereof formulated;
(iii) the cyclodextrin is selected from an α-, β-, and γ-cyclodextrin or a modified form thereof;
(iv) a buffer is optionally present and when present the pH of the formulation is from about pH5.5 to about pH8.0 and in the absence of buffer, the pH is from about pH3 to about pH9.5;
(v) the formulation is sterilizable;
(vi) intravenous injection of the formulation induces less pain than from a propofol formulation;
(vii) the therapeutic index of the formulation is greater than 5;
(viii) the formulation can be stored in a plastic container; and
(ix) the formulation can initiate rapid induction of anaesthesia to surgical levels with similar or more rapid wakening time compared to propofol.

In a particular embodiment, an anaesthetic or sedative formulation is provided comprising a sulfoalkyl ether or sulfoalkyl ether-alkyl ether dextrin, a neuroactive steroid anaesthetic such as alphaxalone or alphadolone and one or more co-polymers such as HPMC, PVP and/or CMC.

In a particular embodiment, the neuroactive steroid anaesthetic is formulated with a sulfoalkyl ether dextrin such as (7) sulfobutyl ether β-cyclodextrin.

The present invention further contemplates a method for formulating an anaesthetic or sedative composition, the method generating a host/guest composition comprising a cyclodextrin and a neuroactive steroid. In an embodiment, the cyclodextrin is a sulfoalkyl ether or sulfoalkyl ether-alkyl ether dextrin such as (7) sulfobutyl either β-cyclodextrin or sulfobutyl ether-alkyl ether β-cyclodextrin. Other cyclodextrins include β-cyclodextrin sulfobutyl ether-ethyl ether, β-cyclodextrin sulfobutyl ether (flat), γ-cyclodextrin sulfobutyl ether, α-cyclodextrin sulfobutyl ether and their sodium salts.

The present invention is further described by the following non-limiting Examples. When a neuroactive steroid anaesthetic is formulated with a cyclodextrin, it is referred to as "neuroactive steroid anaesthetic$_{CD}$". An example is Phaxan$_{CD}$, which comprises alphaxalone formulated with a cyclodextrin which in this case is (7) sulfobutyl ether β-cyclodextrin. Other examples include pregnanolone$_{CD}$ and alphadolone$_{CD}$.

EXAMPLE 1

Anaesthetic Effects of Alphaxalone in 30% w/v (7) Sulfobutyl Ether β-Cyclodextrin Alphaxalone was formulated as 6 ml clear colorless liquid containing:
Alphaxalone 60 mg (10 mg/ml);
(7) sulfobutyl ether β-cyclodextrin 1800 mg;
Saline (0.9% w/v) 6 ml.

This is a molar complexation ratio of alphaxalone to (7) sulfobutyl ether β-cyclodextrin of 1:4.6. Male Wistar rats (weight [wt] 270-315 g) with indwelling jugular intravenous catheters were put in a Perspex restrainer and given the injections with the attached observations upon release from the restrainer shown in Table 1.

TABLE 1

Effects of alphaxalone formulation on Wistar rats

| TIME MINUTES | PRC447 | PRC 446 | PRC 468 | PRC 461 | PRC 448 | PRC 469 | PRC 455 |
|---|---|---|---|---|---|---|---|
| | C 5 | C 10 | C 15 | C 20 | C 20 | C 25 | C 100 |
| 0 | s | | | | | S | TP- |
| 1 | s | | | RR- | TP- | S | TP- |
| 2 | s | s | S | RR- | TP- | RR- | TP- |
| 3 | s | s | S | TP- | TP- | RR- | TP- |
| 4 | s | RR- | RR- | TP- | TP- | RR- | TP- |
| 5 | REC | RR- | RR- | TP- | TP- | RR- | TP- |
| 6 | | RR- | RR- | TP- | TP- | RR- | TP- |
| 7 | | RR+ | RR- | TP- | TP- | RR- | TP- |
| 8 | | s | RR- | TP- | TP- | RR- | TP- |
| 9 | | s | RR- | TP- | TP- | RR- | TP- |
| 10 | | s | RR- | TP- | TP- | RR- | TP- |
| 11 | | s | RR- | TP- | TP+ | RR+ | TP- |
| 12 | | s | RR+ | TP+ | RR- | RR+ | TP- |
| 13 | | s | S | RR- | RR- | RR+ | TP- |
| 14 | | ss | S | RR- | S | RR+ | TP- |

KEY
S sedated
RR+ returned righting reflex
RR- lost righting reflex
TP+ normal tail pinch response
TP- none or minimal response to tail pinch
REC recovered
no sedation
C = cyclodextrin formulation [5, 10, 15, 20, 25 and 100 mg/kg]

The rats given 25 and 100 mg/kg body weight had recovered by 60 minutes; they did not die or suffer any adverse effects at these doses. In these experiments, it can be seen that intravenous injection of alphaxalone 10 mg/ml dissolved in (7) sulfobutyl ether β-cyclodextrin caused loss of consciousness at doses above 10 mg/kg and there was a dose related anaesthetic effect with a wide safety margin; rats that received 25 and 100 mg/kg body weight (two times and ten times the anaesthetic dose) did not die indicating a wide safety margin for the preparation. This is clearly different from a formulation of alphaxalone in hydroxypropyl β-cyclodextrin. Such a preparation (AlfaxanCD-RTU) made by Jurox Pty, Newcastle NSW Australia has a published $LD_{50}$, the dose of alphaxalone that causes death in 50% of rats when given intravenously, of 19 mg/kg body weight, a figure very significantly below that shown here for alphaxalone formulated in sulfobutyl ether β-cyclodextrin [Alfaxan CD-RTU Material safety Data Sheet; Jurox Pty, Newcastle NSW Australia].

EXAMPLE 2

Pharmacokinetics in the Rat

Two groups of ten rats with implanted internal jugular intravenous and carotid intraarterial catheters receive bolus intravenous injections via the jugular vein of 10 mg/kg body weight of (7) sulfobutyl ether β-cyclodextrin formulation of alphaxalone (n=10 rats) or a mixture of alphaxalone and alphadolone in CremophorEL (a polyethoxylated Caster oil), 1.1 ml/kg (n=10 rats). Blood taken from the carotid artery or tail at a number of time intervals after this injection is analyzed for alphaxalone blood levels. These are fitted to a three compartment pharmacokinetic model and mean±sem for key parameters are calculated for both preparations of steroid anaesthetic.

It is expected that there will be no significant difference between the PK parameters calculated for the (7) sulfobutyl ether β-cyclodextrin formulation and the Althesin (Registered Trademark) formulation. This would indicate that the new formulation is expected to behave in a similar fashion to the way Althesin (Registered Trademark) has behaved in the past, particularly with respect to doses needed for anaesthesia and sedation and also the speed of recovery. A sample table of blood levels that can be expected from these experiments appears in Table 2.

TABLE 2

| Variable | Units | |
|---|---|---|
| Duration of Anaesthesia | Min | 35.0 [9.0] |
| AUC | Min * mg/L | 58.6 [11.7] |
| $t_{1/2 \, (elim)}$ | Min | 38.2 [5.6] |
| $Cl_T$ | mL/min/kg | 38.0 [8.2] |
| $V_c$ | L/kg | 0.5 [0.3] |
| $V_{dss}$ | L/kg | 1.8 [0.6] |

EXAMPLE 3

Anaesthetic Effects of Alphaxalone in (7) Sulfobutyl Ether β-Cyclodextrin Compared with Alphaxalone as Althesin (Registered Trademark) and Propofol Male Wistar rats (wt 150-220 g weight) were implanted with indwelling internal jugular vein intravenous catheters under halothane anaesthesia. Twenty four hours later each rat received an intravenous injection from a range of doses of either: propofol (10 mg/ml in 10% w/v Intralipid emulsion; Diprivan [Registered Trademark]); Althesin [Registered Trademark] (alphaxalone 9 mg/ml plus alphadolone acetate 3 mg/ml in 20% w/v CremophorEL); or $Phaxan_{CD}$ (alphaxalone 10 mg/ml in a 1:2 molar complexation ratio with Captisol (Registered Trademark)—(7) sulfobutyl ether β-cyclodextrin). The following were assessed at regular time intervals after the intravenous injection:

1. righting reflex: scored as: 1 normal; 2 slow; 3 some attempt; 4 none—this was a measure of onset and duration of unconsciousness;
2. tail pinch response: scored as: 1 normal; 2 weak; 3 just present; 4 none—this was a measure of onset and duration of surgical anaesthesia; and
3. time to when the rat was able to walk on the rotarod (a rotating cylinder) measured in seconds: the maximum normal run time is 120 s in non sedated rats—attaining this value was a measure of time taken to attain full recovery from the sedating effects of the anaesthetic injections.

Results from groups of ten rats treated with the same anaesthetic and dose were combined for statistical purposes. Rats that attained a score of 4 for loss of righting reflex were deemed to have lost consciousness and those that scored a 4 for loss of tail pinch response were deemed to be surgically anaesthetized. The number of rats in each group of 10 similarly treated animals that scored 4 were subjected to probit regression analysis using SPSS Statistics 18 to produce graphs of probit value v log dose (probit plot) and also to calculate the estimated dose that caused anaesthesia in 50 and 95% of subjects ($AD_{50}$ and $AD_{95}$, respectively) for unconsciousness (righting reflex measurements) and surgical anaesthesia (tail pinch responses). The rotarod walking times were also plotted for each dose and treatment. This was used as a measurement of complete recovery. The results are shown in FIGS. 1a through 1f, rotarod performance for each anaesthetic, n=10 rats per dose.

Table 3 below summarises the results of this series of experiments. It can be seen that $Phaxan_{CD}$ is equipotent with Althesin (Registered Trademark) in causing unconsciousness and surgical anaesthesia and both are more potent than propofol in this respect. Recovery from unconsciousness caused by $Phaxan_{CD}$ is just as fast as with propofol. However, recovery from $Phaxan_{CD}$ is slightly slower than propofol but faster than Althesin (Registered Trademark) if the depth of anaesthesia is taken to a surgical level. Control experiments revealed that the vehicles given alone intravenously, 20% CremophorEL, 10% Intralipid and 13% Captisol had no sedating or anaesthetic effects.

EXAMPLE 4

Lethal Dose Finding for Alphaxalone Anaesthetic Preparations

Figure 2:
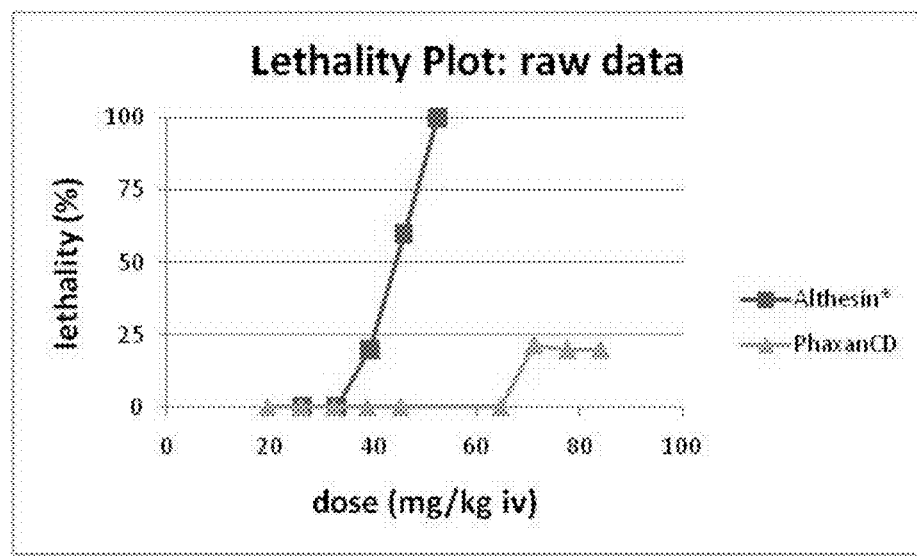
FIG. 2 is a graphical representation of lethal dosing of two alphaxalone preparations [Phaxan$_{CD}$ and Althesin in rats].

This series of experiments was undertaken to determine the $LD_{50}$ and $LD_{95}$ doses for alphaxalone formulated in CremophorEL [Althesin (Registered Trademark)] and (7) sulfobutyl ether β-cyclodextrin ($Phaxan_{CD}$); i.e., the doses of alphaxalone in Captisol (Registered Trademark) that caused 50% and 95% of subjects to die. Male Wistar rats (wt 150-220 g weight) were implanted with indwelling internal jugular vein intravenous catheters under halothane anaesthesia. Twenty four hours later each rat received an intravenous injection from a range of doses of either: Althesin (Registered Trademark) (alphaxalone 9 mg/ml plus alphadolone acetate 3 mg/ml in 20% CremophorEL); or $Phaxan_{CD}$ (alphaxalone 10 mg/ml in a 1:2 molar complexation ratio with Captisol (Registered Trademark)—(7)sulfobutyl ether β-cyclodextrin). The number of rats that died was recorded for each group of 10 rats given the same dose of drug. Results from groups of ten rats treated with the same anaesthetic and dose were combined for statistical purposes. The graph of the raw data is shown in FIG. 2 [% rats died in each dosage group v dose].

Figure 3:
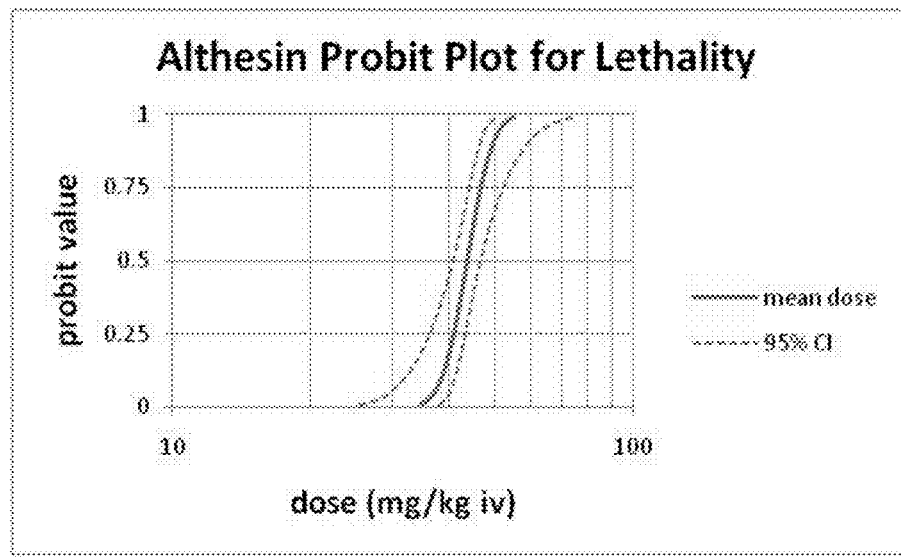
FIG. 3 is a graphical representation of a probit plot for lethality dosing of an Althesin preparation in rats.

At doses of alphaxalone between 50 and 60 mg/kg all the rats in the Althesin (Registered Trademark) groups died whereas none died in the $Phaxan_{CD}$ groups that received the same doses of alphaxalone. The lethality values for $Phaxan_{CD}$ showed a ceiling at 20%; no more than 20% rats died even if the dose of alphaxalone administered as $Phaxan_{CD}$ were increased. The percentages of rats that died in all the different dosage treatment groups were subjected to a probit regression analysis using SPSS Statistics 18 and the probit values were plotted on a graph against the log dose of anaesthetic; this is called a probit plot. This is shown in FIG. 3.

The probit plot for Althesin (Registered Trademark) was used to calculate the dose of alphaxalone in this formulation that caused death in 50% and 95% rats; the $LD_{50}$ and $LD_{95}$ respectively). These values were 43.6 mg/kg [$LD_{50}$] and 51.5 mg/kg [$LD_{95}$]. As the dose of alphaxalone was increased the number of rats that died increased in proportion when the

TABLE 3

|  |  | Althesin (Registered Trademark) | $Phaxan_{CD}$ | propofol | ANOVA with Tukey post hoc |
|---|---|---|---|---|---|
| minimum dose causing all 10 rats to lose righting reflex mg/kg |  | 5 | 5 | 10 |  |
| $ED_{50}$ dose for loss of righting reflex mg/kg |  | 2.95 | 2.79 | 4.63 |  |
| $ED_{95}$ dose for loss of righting reflex mg/kg |  | 4.39 | 4.26 | 8.4 |  |
| minimum dose causing all 10 rats to lose tail pinch response mg/kg |  | 15 | 15 | 15 |  |
| $ED_{50}$ dose for loss of tail pinch response reflex mg/kg |  | 6.46 | 6.56 | 8.4 |  |
| $ED_{95}$ dose for loss of tail pinch response mg/kg |  | 14.09 | 8.56 | 14.46 |  |
| duration of loss of righting reflex at dose causing all 10 rats to lose righting reflex (minutes) | mean = | 3.6 | 1.9 | 2.5 | not significant ANOVA p = 0.0527 |
|  | SD = | 2.18 | 0.84 | 1.15 |  |
| duration of loss of tail pinch response at dose causing all 10 rats to lose tail pinch response (minutes) | mean = | 13.45 | 4.65 | 4.05 | Althesin vs $Phaxan_{CD}$ *** P < 0.001; |
|  | SD = | 3.9 | 2.55 | 1.28 | Althesin vs propofol *** P < 0.001; $Phaxan_{CD}$ vs propofol ns P > 0.05 |
| time (minutes) to overall (complete) recovery of rotarod performance after minimum anaesthetic dose (lost RR) | mean = | 19.9 | 17 | 16 | Althesin vs $Phaxan_{CD}$ ns P > 0.05; |
|  | SD = | 3.93 | 2.16 | 1.89 | Althesin vs propofol * P < 0.05; $Phaxan_{CD}$ vs propofol ns P > 0.05 |
| time (minutes) to overall (complete) recovery of rotarod performance after minimum surgical anaesthetic dose (lost tail pinch) | mean = | 39 | 32.5 | 23.1 | Althesin vs $Phaxan_{CD}$ *** P < 0.001; |
|  | SD = | 3.16 | 3.54 | 3.25 | Althesin vs propofol *** P < 0.001; $Phaxan_{CD}$ vs propofol *** P < 0.001 |

It can be concluded from this set of experiments that:

$Phaxan_{CD}$ is an effective intravenous anaesthetic causing fast onset of general anaesthesia after intravenous injection.

It is equipotent with Althesin and twice as potent as propofol.

alphaxalone was given as Althesin (Registered Trademark). By contrast there was a ceiling effect of the lethality of the alphaxalone in (7) sulfobutyl ether β-cyclodextrin ($Phaxan_{CD}$) formulation. The alphaxalone was much less assessed by lethality compared with alphaxalone formulated toxic as with CremophorEL (Althesin [Registered Trademark]). A dose of 52 mg/kg alphaxalone as Althesin (Registered Trademark) caused all 10 rats in that group to die but 64 mg/kg alphaxalone caused no deaths in the 10 rats which received that dose of alphaxalone formulated with (7) sulfobutyl ether β-cyclodextrin (Phaxan$_{CD}$). Furthermore, unlike the probit plot for Althesin (Registered Trademark), which showed a direct proportional relationship of increasing lethality with increasing dose, alphaxalone formulated in (7) sulfobutyl ether β-cyclodextrin (Phaxan$_{CD}$) showed a ceiling effect for lethality; when the dose of alphaxalone in this preparation was increased to 71, 78 and then 84 mg/kg only 20% of rats died in each group. Thus, it was not possible to find the dose of alphaxalone in this formulation that caused death in 50% and 95% rats (the LD$_{50}$ and LD$_{95}$, respectively). In any event, both of these values are greater than 84 mg/kg which is more than double the equivalent values for Althesin (Registered Trademark) and four times the value of the LD$_{50}$ for alphaxalone formulated in hydroxypropyl β-cyclodextrin manufactured by Jurox [Alfaxan CD-RTU Material Safety Data Sheet. Jurox Pty, Newcastle NSW Australia].

These results make the therapeutic index (ratio of dose that causes death in 50% subjects (LD$_{50}$) divided by the dose that causes anaesthesia in 50% subjects (the AD$_{50}$) to be 14.8 for Althesin (Registered Trademark) and >30.2 for alphaxalone formulated in (7) sulfobutyl ether β-cyclodextrin (Captisol [Registered Trademark] Phaxan$_{CD}$). This difference is not due to differences in toxicity of the excipients. Table 4 below shows the results of experiments in 10 rats with indwelling jugular intravenous catheters. Five rats were given a 20% solution of Cremophor EL intravenously and another five rats were given a solution of (7) sulfobutyl ether β-cyclodextrin, both being administered at a dose and volume equal to that administered in the experiments above at the highest dose of alphaxalone. Neither excipient caused death in any rat indicating that the difference in the safety/lethality of the two formulations of alphaxalone was not due to dose related toxicity of the excipients.

TABLE 4

| n/10 died | vehicle | dose = ml/kg |
|---|---|---|
| 0 | 13% Captisol | 9.0 |
| 0 | 20% Cremophor EL | 4.6 |

EXAMPLE 5

Demonstration of the Limitation of Alphaxalone Toxicity by Captisol [Registered Trademark] (Sulfobutyl Ether β-cyclodextrin)

Since the potency in causing anaesthesia is the same for a bolus dose of alphaxalone whether given in 20% CremophorEL (Althesin [Registered Trademark]) or in (7) sulfobutyl ether β-cyclodextrin (Phaxan$_{CD}$), then the ceiling effect for toxicity must be related to the (7) sulfobutyl ether β-cyclodextrin when higher doses of alphaxalone in the (7) sulfobutyl ether β-cyclodextrin formulation are administered. Such a property has not been described for intravenous anaesthetics before. Furthermore, this property has not been described before for alphaxalone formulated in other cyclodextrins.

In order to test whether the low toxicity of Phaxan$_{CD}$ was due to the Captisol excipient, twenty rats with indwelling jugular intravenous catheters were divided into two groups of 10 rats each. They were all given intravenous injections of alphaxalone formulated in 20% Cremophor at a dose that had, in previous experiments reported in example 4, caused all rats to die (Althesin [Registered Trademark]; alphaxalone dose 52.5 mg/kg iv—this equals 16 times the AD$_{95}$ for Althesin (Registered Trademark) at which it is expected a very high proportion or all rats will die). Sixty seconds before the Althesin (Registered Trademark) injection a premedication injection was given:

group 1 (10 rats) received 5.3 mls/kg 0.9% sodium chloride solution 60 seconds before 52.5 mg/kg alphaxalone as Althesin (Registered Trademark);

group 2 (10 rats) received 5.3 mls/kg 13% solution of (7) sulfobutyl ether β-cyclodextrin in 0.9% sodium chloride solution 60 seconds before 52.5 mg/kg alphaxalone as Althesin (Registered Trademark).

The number of rats that died in each group was recorded shown in Table 5. All 20 rats were anaesthetized by the injection of 52.5 mg/kg alphaxalone as Althesin (Registered Trademark). However, the presence of (7) sulfobutyl ether β-cyclodextrin caused a statistically and clinically significant reduction in the mortality caused by the alphaxalone.

TABLE 5

ALL RATS THAT SURVIVED WERE ANAESTHETISED >1 HOUR
premed given 60 s before Althesin @ 16 x AD95

| premed volume = 5.25 mls/kg | n died | n did not die |
|---|---|---|
| SALINE PREMED | 8 | 2 |
| SBECD7 PREMED | 2 | 8 |

Study Of The Effect of Captisol on the Death Rate of Althesin
Fisher's Exact Test
The two-sided P value is 0.0230, considered significant.
The row/column association is statistically significant.

This is a much unexpected result.

EXAMPLE 6

The Effect on Sleep Times of Repeated Dosing with Phaxan$_{CD}$

The mechanism responsible for the (7) sulfobutyl ether β-cyclodextrin in causing the ceiling effect on alphaxalone toxicity is unknown. It is known that alphaxalone is very poorly soluble in water and thus the vast majority of alphaxalone molecules are complexed with the cyclodextrin molecules in the ratio of 1:2 (the complexation ratio). It is known that some of the alphaxalone will dissociate from the cyclodextrin complex when Phaxan$_{CD}$ is injected intravenously. The question posed by the unique property of the alphaxalone sulfobutyl ether cyclodextrin complex exhibiting a ceiling effect for toxicity is whether this is caused by limiting the amount of alphaxalone released from the complex or whether there occurs a "mopping up" of alphaxalone molecules that might otherwise penetrate the brain to cause toxicity, by excess uncomplexed cyclodextrin molecules freed up by alphaxalone metabolism by the liver. The effect of the latter would be predicted to cause a progressive decrease in the level of free alphaxalone as the concentration of uncomplexed sulfobutyl ether cyclodextrin increased as a result of:
liver metabolism of the alphaxalone;
more doses of Phaxan$_{CD}$ being administered thereby making more uncomplexed cyclodextrin available.

If this were the case one would predict tolerance to repeated doses of alphaxalone formulated in (7) sulfobutyl ether β-cyclodextrin i.e., repeated injections of Phaxan$_{CD}$ would cause progressively less sedation and anaesthetic effect.

Figure 4:
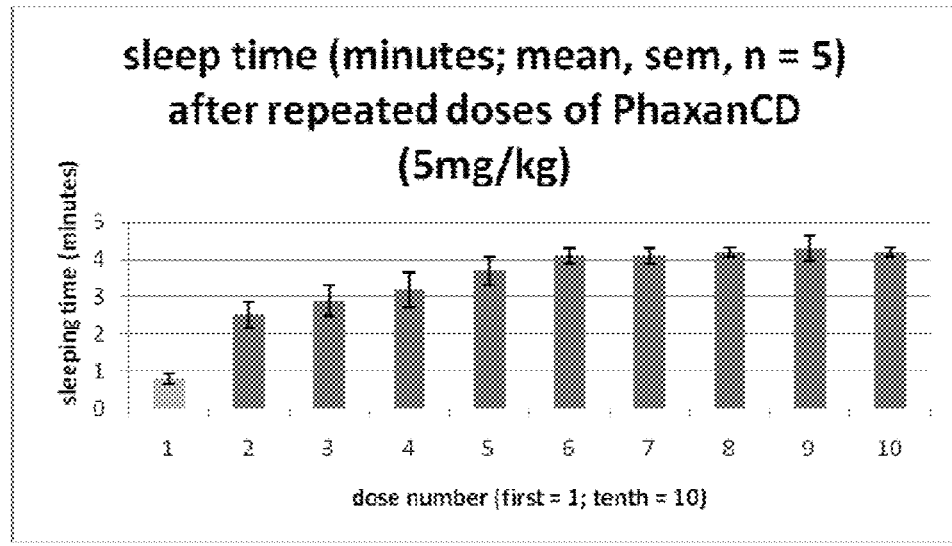
FIG. 4 is a graphical representation of sleep time in rats using repeated doses of Phaxan$_{CD}$ (alphaxalone in a 1:2 molar complexation ratio with (7) sulfobutyl ether β-cyclodextrin).

In order to test this five rats with indwelling jugular intravenous catheters were given repeated injections of the minimum dose of alphaxalone in (7) sulfobutyl ether β-cyclodextrin (5 mg/kg Phaxan$_{CD}$) that had caused 10/10 rats to be anaesthetized as judged by complete loss of righting reflex. The time was measured for each rat to begin recovery of righting reflex (progress from a score of 4 to a score of 3 in the righting reflex as described in example 2 above) and then another dose of 5 mg/kg Phaxan$_{CD}$ was given. The time to the beginning of recovery of the righting reflex after the second dose of anaesthetic was measured and then another dose of 5 mg/kg Phaxan$_{CD}$ was administered iv and the process was repeated eight more times. The progressive recovery times for the first to the tenth doses are shown in the histogram (FIG. 4) and table 6 below as means (sem) for those five rats. It can be seen that there was a significant progressive increase in recovery times after each of the first four doses. Further doses 5-10 caused no further significant increase and more importantly, no decrease, in sleeping time. These results indicate that the alphaxalone toxicity ceiling effect caused by the (7)sulfobutyl ether β-cyclodextrin is probably due to the controlled release of the alphaxalone from the complex at a rate sufficient to cause anaesthesia but no greater than that, no matter how much of the complex is given. This is a unique balance between the chemical relationship of the alphaxalone and the (7) sulfobutyl ether β-cyclodextrin, the low solubility of the alphaxalone in water environments, including biological fluids, the amount of alphaxalone needed to penetrate the brain to cause anaesthesia and the pharmacokinetics of alphaxalone. The results are shown in FIG. 4 and Table 6. None of this was expected nor could have been predicted from prior art.

TABLE 6

| dose number | sleep time (mins) | |
|---|---|---|
| | mean | sem |
| first | 0.8 | 0.14 |
| second | 2.5 | 0.35 |
| third | 2.9 | 0.41 |
| fourth | 3.2 | 0.45 |
| fifth | 3.7 | 0.38 |
| sixth | 4.1 | 0.21 |
| seventh | 4.1 | 0.21 |
| eighth | 4.2 | 0.14 |
| ninth | 4.3 | 0.34 |
| tenth | 4.2 | 0.14 |

One way ANOVA [Tukey Kramer post hoc] applied to the data of sleep times after X 10 repeated dosing of 5 rats with Phaxan$_{CD}$ 5 mg/kg revealed that there was a progressive statistically significant increase in sleeping time from the first to the second, second to the third and third to the fourth but no increase in sleeping times thereafter. Furthermore it is important to note that there was not a progressive decrease in sleeping times that would be predicted if the mechanism for low toxicity and the ceiling effect of Phaxan$_{CD}$ was due to uncomplexed "free" sulfobutyl ether cyclodextrin [Captisol (Registered Trademark)] mopping up alphaxalone from the blood. If that were the case then the amount of free uncomplexed Captisol would increase as more doses were given and as alphaxalone was metabolized by the liver so leading to a progressive increase in free uncomplexed Captisol as the repeated exposure experiment progressed. If the alphaxalone were mopped up by this then one would expect less sleeping time with each successive dose. On the contrary the sleep time increased with each of the first four doses and then remained constant thereafter with each subsequent dose.

EXAMPLE 7

Ceiling Toxicity

The following assumption is made:
A. that intravenous injection of Althesin (Registered Trademark) leads to an instantaneous dispersal of alphaxalone in the plasma but, since anaesthesia is caused by drug injection in one circulation and also alphaxalone is cleared from the blood by the liver on first pass, the level achieved by the mixing in the plasma will only reach 30% of the theoretical maximum assuming instantaneous mixing.

The following is considered:
1. alphaxalone is soluble in water to 0.03 mg/ml;
2. alphaxalone is 35% protein bound in plasma;
3. plasma volume is 31 ml/kg in rat (Davies and Morris, *Pharmaceutical Research*, 10(7):1093-95, 1993);
4. both Althesin (Registered Trademark) and Phaxan$_{CD}$ have alphaxalone concentrations of 10 mg/ml;
5. for induction of anaesthesia Althesin (Registered Trademark) and Phaxan$_{CD}$ are equipotent; a minimum of 4.3 mg/kg alphaxalone by either preparation cause sleep in most (95%) rats;
6. after an initial bolus injection a drug preparation will equilibrate with the plasma volume during the first sleep cycle but later the drug will disperse into the extracellular fluid [ECF] which is=297 ml/kg (Davies and Morris, 1993 supra);
7. Captisol is distributed to ECF and restricted to this space; and
8. Alphaxalone is only released from the Captisol into an aqueous environment if the level of free alphaxalone in the aqueous environment is less than saturation i.e., <0.03 mg/ml [fact 1].

It is proposed herein that:
I. From A and 5 above, the plasma level of drug needed to cause sleep=dose administered as Althesin/plasma volume=4.3/31=0.14 mg/ml.
II. Applying A, the plasma concentration is expected to be 30% of this when the blood has circulated to mix the drug effectively=0.046 mg/ml.
III. From this, the level of free unbound alphaxalone in the plasma associated with anaesthesia induction after a single iv bolus injection=65% of total (from fact 2)=0.045×0.65=0.03 mg/ml.
IV. Proposition III above is exactly the known solubility of alphaxalone in water.
V. Combining points 5 and 8 with proposition IV, it is proposed herein that the first induction dose of Phaxan$_{CD}$ caused anaesthesia by releasing all of the alphaxalone from the complex just achieving the anaesthetic level and free alphaxalone saturation level.
VI. When the second dose of anaesthetic was administered in Example 9 the rat was starting to recover from the anaesthetic because some free alphaxalone had been metabolized by the liver, some free alphaxalone had been redistributed to the ECF and some of the Captisol containing alphaxalone had also redistributed to the ECF. Thus, the free alphaxalone level fell and alphaxalone left the brain so causing awakening. Thus, a further dose was given. Unlike the first dose, there was still alphaxalone in the blood so only some of the alphaxalone was released from the complex to bring the free alphaxalone level back to 0.03 mg/ml; the brain is reloaded and sleep follows.

VII. However, sleep follows for a longer time after the second dose and the third and also the fourth until the ECF is loaded with 0.03 mg/ml alphaxalone and alphaxalone/Captisol complex [points 6 and 7]. After that further doses of Captisol merely top up the blood level of free alphaxalone and maintain it until hepatic metabolism has cleared that dose of alphaxalone.

VIII. Once the level of free alphaxalone reaches 0.03 mg/ml, the brain is anaesthetized. The brain will only absorb more alphaxalone if the level of free alphaxalone increases. This is possible with Althesin (Registered Trademark) and death ensues when 15 times the anaesthetic dose of that drug is administered as a bolus leading to a theoretical free alphaxalone level of 0.45 mg/ml. In contrast, when that dose of alphaxalone is given as Phaxan$_{CD}$, in a complex with Captisol (Registered Trademark), the alphaxalone is not released from the complex once the level of free alphaxalone reaches 0.03 mg/ml [point 1]. This explains the ceiling effect on lethality with alphaxalone when formulated in 13% sulfobutyl-7-ether β-cyclodextrin.

IX. Since no further increase in sleep time occurs after the fifth dose of 5 mg/kg Phaxan$_{CD}$ and subsequent doses of the same magnitude, then the clearance of alphaxalone must be in equilibrium with the dose administration rate. The equilibrium clearance of alphaxalone is therefore 5 mg/kg/4.2 min. Since the concentration in plasma is approximately 0.04 mg/ml then the plasma clearance rate at equilibrium=$((5\pm4.2)\div0.04)$=30 mls/kg/min. This is within known values of hepatic blood flow (Davies and Morris, 1993 supra). It is well known that alphaxalone is primarily cleared from plasma by first pass hepatic metabolism.

X. The latter implies that this particular formulation of alphaxalone in sulfobutyl ether β-cyclodextrin controls the level of free unbound anaesthetic that penetrates the brain up to but not above a level that causes anaesthesia; the Captisol cannot release any more compound above the level at which plasma water is saturated with alphaxalone and thus higher blood levels that would cause toxicity are not achieved.

This property has not been described for intravenous anaesthetics or intravenous cyclodextrins before. It arises from a unique set of circumstances not described or previously discovered:

1. A unique host:guest interaction. The evidence for this is the fact that the same guest [alphaxalone] formulated in another host cyclodextrin (Alfaxan$_{CD}$-RTU; hydroxypropyl β-cyclodextrin—the Jurox preparation) does not have a ceiling on toxicity with a quoted $LD_{50}$ of 19 mg/kg iv in rats, a dose which is 75% less than the dose of alphaxalone in the (7) sulfobutyl ether β-cyclodextrin which only causes 20% lethality;
2. The guest is a compound that causes anaesthesia at a free drug level which is equal to its aqueous solubility; and
3. The guest is a compound that has a high therapeutic index so that the free drug level is well below the toxic level.

EXAMPLE 8

Pregnanolone Formulation

The neuroactive steroid anaesthetic pregnanolone was mixed with 13% w/v sulfobutyl ether β-cyclodextrin (Captisol [Registered Trademark]) in 0.9% saline to form pregnanolone$_{CD}$. The pregnanolone dissolved incompletely at a concentration of 10 mg/ml, and unlike alphaxalone, it only went into solution after 4 hours of continuous stiffing. The solution was opalescent. This observation indicates that all neuroactive steroids do not interact with (7) sulfobutyl ether β-cyclodextrin in the same way. Fifteen male Wistar rats (150-200 g weight) with surgically-implanted internal jugular intravenous catheters were used for these experiments in which they received intravenous pregnanolone$_{CD}$ injections: 2.5 mg/kg (n=5); 5 mg/kg (n=5); and 10 mg/kg (n=5).

Figure 5:
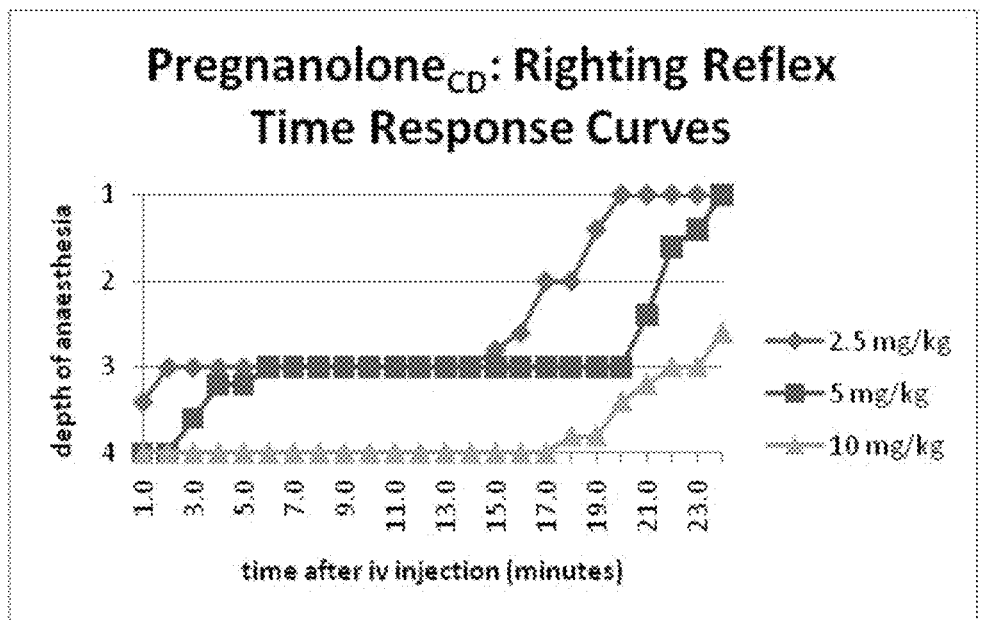
FIG. 5 is a graphical representation of righting reflex time response curves in rats using pregnanolone in a (7) sulfobutyl ether β-cyclodextrin.

They were assessed for anaesthesia by the righting reflex which was scored: 1 normal; 2 slow; 3 some attempt; 4 none. A score of 4 means that a state of unconsciousness (anaesthesia) has been achieved. FIG. 5 below shows the results from this test for the rats in the three groups that received 2.5, 5 and 10 mg/kg pregnanolone. Results shown are means of the readings from all 5 rats at each time point after intravenous injection of pregnanolone.

Figure 6:
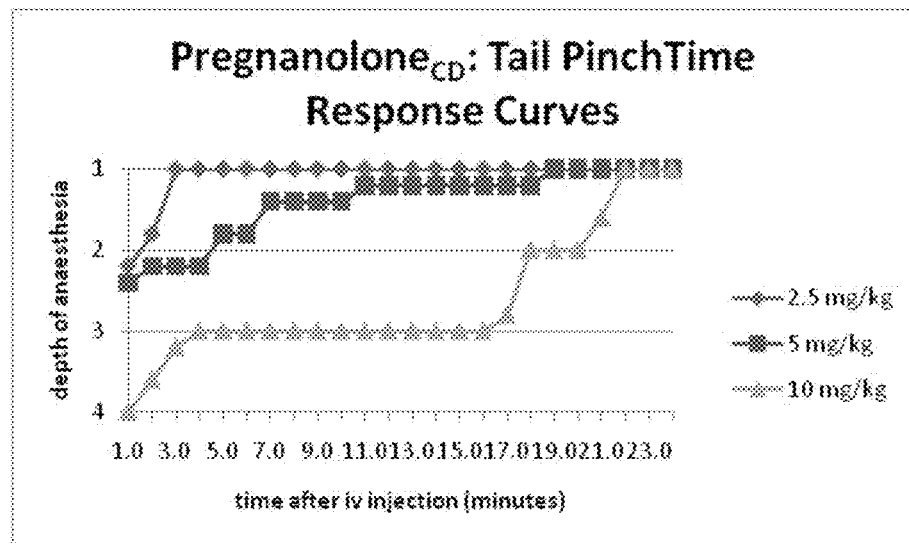
FIG. 6 is a graphical representation of tail pinch time response curve in rats using pregnanolone in a (7) sulfobutyl ether β-cyclodextrin.

The rats were also assessed for surgical anaesthesia using tail pinch responses scored: 1 normal; 2 weak; 3 just present; 4 none. A score of 4 indicates surgical anaesthesia has been achieved. FIG. 6 shows the results from this test for the rats in the three groups that received 2.5, 5 and 10 mg/kg pregnanolone$_{CD}$. Results shown are means of the readings from all 5 rats at each time point after intravenous injection of pregnanolone$_{CD}$.

Figure 7:
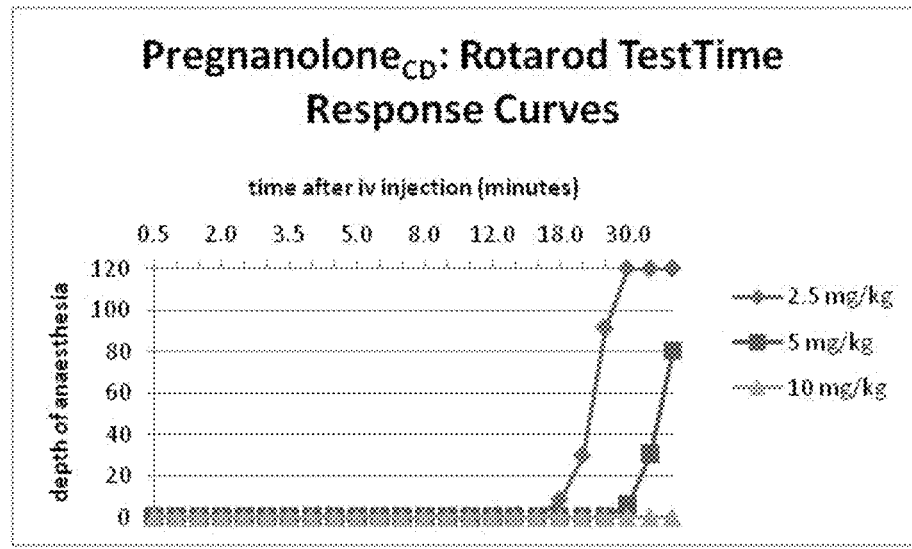
FIG. 7 is a graphical representation of rotarod test time response curve in rats using pregnanolone in a (7) sulfobutyl ether β-cyclodextrin.

Time to complete recovery from the sedating effects of the pregnanolone$_{CD}$ was assessed with the rotarod run time—normal non-sedated rats run on the accelerating rotating drum is 120 seconds; rats are fully recovered when they can walk on the rotarod treadmill for 120 seconds. FIG. 7 below shows the results from this test for the rats in the three groups that received 2.5, 5 and 10 mg/kg pregnanolone$_{CD}$. Results shown are means of the readings from all 5 rats at each time point after intravenous injection of pregnanolone$_{CD}$.

Conclusions

Pregnanolone$_{CD}$ is an intravenous anaesthetic but of long duration. It causes anaesthesia induction immediately after intravenous injection. This effect is dose related and it is possible to cause sufficient CNS depression to lead to surgical anaesthesia.

EXAMPLE 9

Alphadolone Formulation

The neuroactive steroid anaesthetic alphadolone was mixed with 13% w/v sulfobutyl ether β-cyclodextrin (Captisol) in 0.9% w/v saline to form alphadolone$_{CD}$. The alphadolone dissolved completely at a concentration of 10 mg/ml, but unlike alphaxalone, it only went into solution after 4 hours of continuous stirring. This observation indicates that all neuroactive steroids do not interact with (7) sulfobutyl ether β-cyclodextrin in the same way. Fifteen male Wistar rats (150-200 g weight) with surgically-implanted internal jugular intravenous catheters were used for these experiments in which they received intravenous alphadolone$_{CD}$ injections: 10 mg/kg (n=5); 20 mg/kg (n=5); and 40 mg/kg (n=5).

Figure 8:
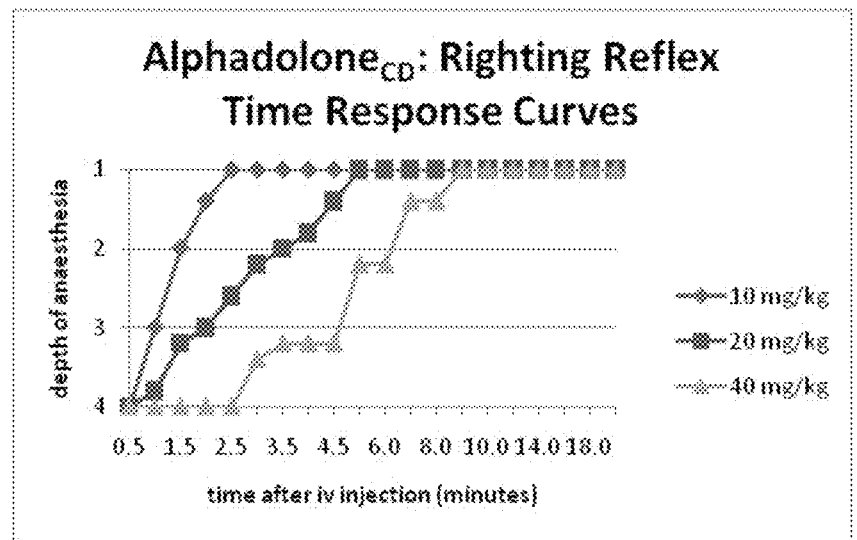
FIG. 8 is a graphical representation of righting reflex time response curves in rats using alphadolone in a (7) sulfobutyl ether β-cyclodextrin.

They were assessed for anaesthesia by the righting reflex which was scored: 1 normal; 2 slow; 3 some attempt; 4 none. A score of 4 means that a state of unconsciousness (anaesthesia) has been achieved. FIG. 8 shows the results from this test for the rats in the three groups that received 10, 20 and 40 mg/kg alphadolone$_{CD}$. Results shown are means of the readings from all five rats at each time point after intravenous injection of alphadolone.

Figure 9:
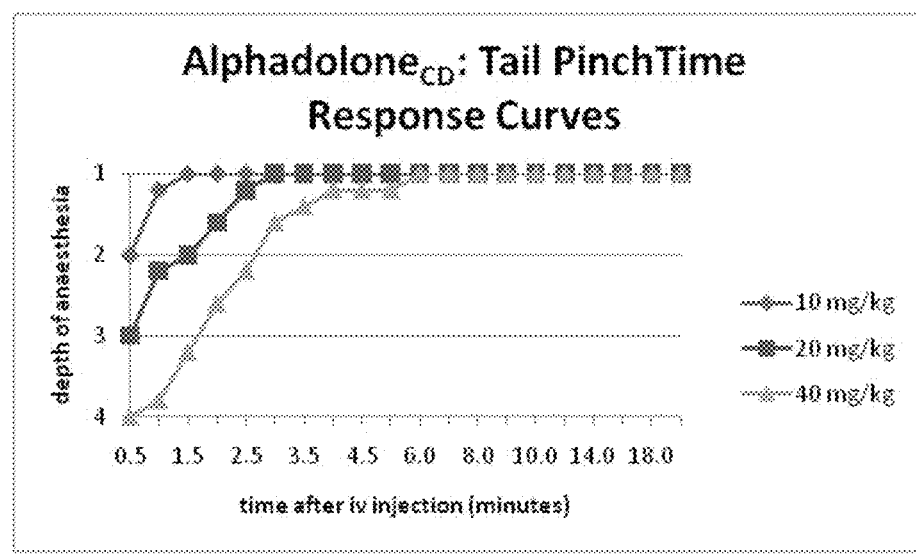
FIG. 9 is a graphical representation of tail pinch time response curves in rats using alphadolone in a (7) sulfobutyl ether β-cyclodextrin.

The rats were also assessed for surgical anaesthesia using tail pinch responses scored: 1 normal; 2 weak; 3 just present;

4 none. A score of 4 indicates surgical anaesthesia has been achieved. FIG. 9 shows the results from this test for the rats in the three groups that received 10, 20 and 40 mg/kg alphadolone$_{CD}$. Results shown are means of the readings from all five rats at each time point after intravenous injection of alphadolone$_{CD}$.

Figure 10:
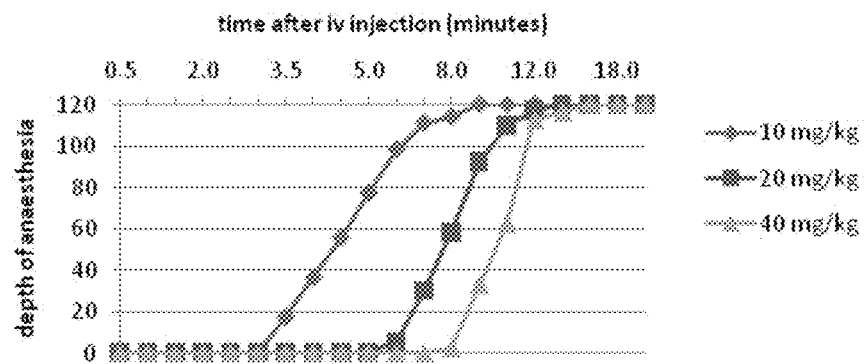
FIG. 10 is a graphical representation of rotarod test time response curves in rats using alphadolone in a (7) sulfobutyl ether β-cyclodextrin.

Time to complete recovery from the sedating effects of the alphadolone$_{CD}$ was assessed with the rotarod run time—normal non-sedated rats run on the accelerating rotating drum is 120 seconds; rats are fully recovered when they can walk on the rotarod treadmill for 120 seconds. FIG. 10 shows the results from this test for the rats in the three groups that received 10, 20 and 40 mg/kg alphadolone$_{CD}$. Results shown are means of the readings from all 5 rats at each time point after intravenous injection of alphadolone$_{CD}$.

Conclusions

Alphadolone$_{CD}$ is an intravenous anaesthetic of short duration. It causes anaesthesia induction immediately after intravenous injection. This effect is dose related and it is possible to cause sufficient CNS depression to lead to surgical anaesthesia.

EXAMPLE 10

Cardiovascular Effects of Phaxan$_{CD}$ Compared with Althesin and Propofol

Figure 11:
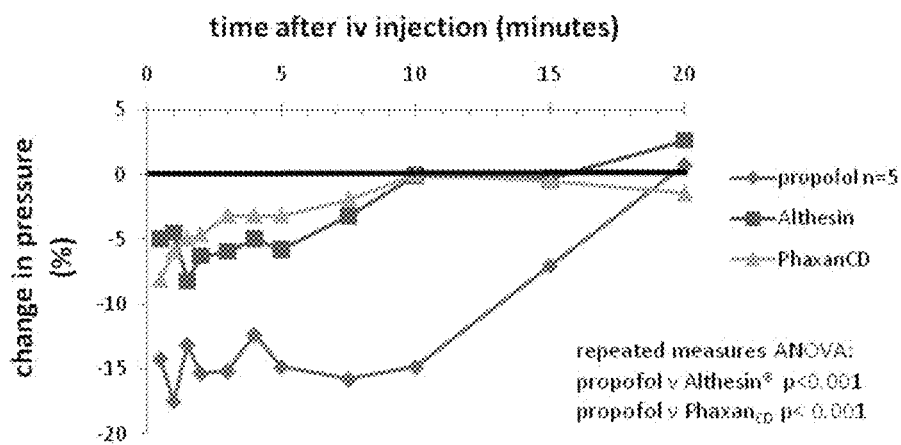
FIG. 11 is a graphical representation of percentage change in mean systolic blood pressure in rats after injection with propofol, Althesin or Phaxan$_{CD}$.
Figure 12:
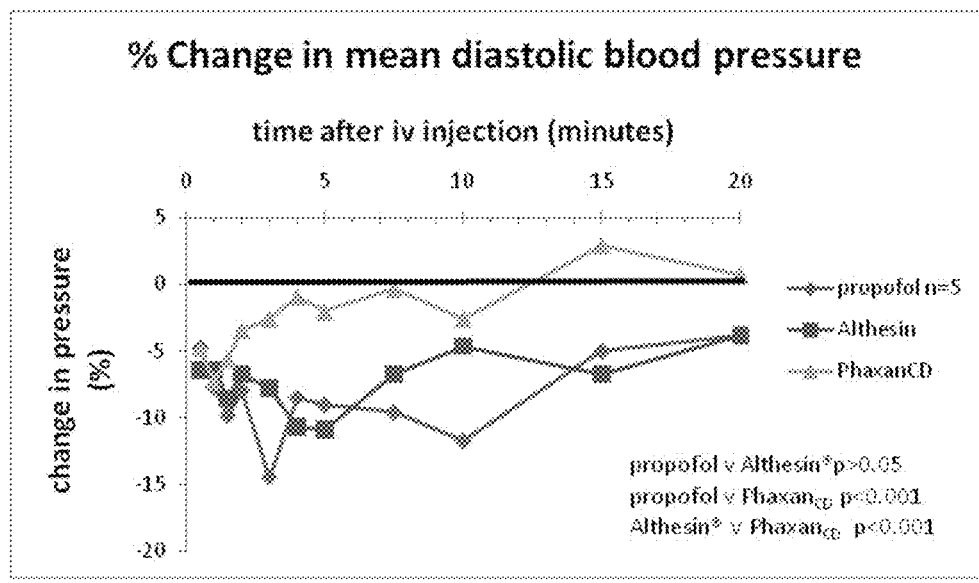
FIG. 12 is a graphical representation of percentage change in mean diastolic blood pressure in rats after injection with propofol, Althesin or Phaxan$_{CD}$.

Fifteen male Wistar rats (150-200 g weight) with surgically-implanted internal jugular intravenous catheters were used for these experiments in which rats in three groups received intravenous injections of equipotent AD$_{95}$ anaesthetic doses of either propofol (6.6 mg/kg; Diprivan 10 mg/ml propofol in 10% Intralipid emulsion), Althesin (3.28 mg/kg alphaxalone; Althesin 9 mg/ml alphaxalone plus 3 mg/ml alphadolone dissolved in 20% CremophorEL), or Phaxan$_{CD}$ (3.23 mg/kg alphaxalone; alphaxalone 10 mg/ml dissolved in Captisol [(7) sulfobutyl ether β-cyclodextrin]13%); n=5 rats per group. Systolic and diastolic blood pressures were measured before and after these injections. Each measurement was calculated as a percentage change from the pre-anaesthetic levels for that rat. FIGS. 11 and 12 show the percentage changes against time for each of the cardiovascular parameters in each treatment group.

Conclusion

Both formulations of alphaxalone (Althesin/20% CremophorEL; Phaxan$_{CD}$/sulfobutyl ether β-cyclodextrin (Captisol [Registered Trademark])) caused less cardiovascular disturbance than an equianaesthetic dose of propofol and in one measure (diastolic blood pressure) the sulfobutyl ether β-cyclodextrin formulation of alphaxalone (Phaxan$_{CD}$) caused less cardiovascular disturbance compared with the CremophorEL preparation (Althesin [Registered Trademark]).

EXAMPLE 11

A Phase ½a Clinical Trial

In these experiments in human volunteers, propofol and (7) sulfobutyl ether β-cyclodextrin/alphaxalone formulation are compared in a double blind manner. Each volunteer is prepared in a fully equipped anaesthetic room. Dosing with either propofol or alphaxalone is determined by a randomization schedule to either propofol or alphaxalone. One anaesthetist designated to give the anaesthetic opens an envelope to find which drug should be given to this patient. The dose of drug is determined from a calculation schedule (see below) relying on the response of the previous patient to the last dose of that drug used—anaesthesia achieved or not based on a measurement of 50 for the bispectral index of the electroencephalogram (BIS value). The patient has an intravenous cannula in the right hand for drug administration and another for blood withdrawal for samples for measurements of blood levels of drug. That arm and the anaesthetist administering the anaesthetic has no communication with the test subject or a second anaesthetist who is in contact with the subject and who is responsible for general care of the subject as well as physiological monitoring. The arm and the drug administering anaesthetist are separated by a curtain from the anaesthetist caring for the subject as well as the subject and anaesthetic nurse present. The first, drug injecting anaesthetist, only communicates that the anaesthetic injection is about to start by ringing a bell and the caring anaesthetist only communicates with the drug administering anaesthetist to say whether a BIS value of 50 or less was achieved after that subject leaves the room at the end of the experiment. Measurements and assessments made:

Subjects weight in kg. This is written on the case record before passing to the administering anaesthetist.

The patient is asked by the caring anaesthetist to report pain on injection and a positive or no report is noted.

Presence or absence of abnormal movements is noted by the caring anaesthetist.4

Time from the ringing of the bell indicating anaesthetic injection to the subject dropping a water-loaded 20 ml syringe held between finger and thumb in the outstretched left arm.

Time from the ringing of the bell indicating anaesthetic injection to loss of verbal contact with the patient and time for that contact to return.

Time from the ringing of the bell indicating anaesthetic injection to the subject losing the eyelash reflex and the time at which that reflex returned.

BIS value and whether a value of 50 or below is achieved and when and for how long after the intravenous injection.

Blood pressure, systolic and diastolic, and pulse rate using non invasive methods measured every 1 minute for 5 minutes, every 2.5 minutes for a further 10 minutes and every 5 minutes thereafter.

Oxygen saturation of the blood measured with a pulse oximeter probe placed on the ear lobe of the left ear. The subject breathes air unless oxygen saturation levels fall below 93% at which time oxygen is given by face mask and anaesthetic circuit. Breathing is assisted if apnoea occurs and persists for longer than 30 seconds. The occurrence of low oxygen saturations and apnoea are noted.

Time to full recovery indicated by normal performance in a digital substitution test Blood taken for analysis of alphaxalone blood levels at 0.5, 1.0, 1.5, 2, 5 10, 15, 30 and 60 minutes after anaesthetic injection.

Blood taken before the experiment, one hour after the experiment and 24 hours and one week later for:

Full haematological analysis.

Hepatic function tests.

Renal function tests.

Dose Schedule

When the envelope is opened by the administering anaesthetist the randomized instruction will be to give propofol or alphaxalone. If this is the first subject to receive the drug they are given: propofol 2 mg/kg; alphaxalone 0.5 mg/kg.

The dosing for the next patient to receive that drug is determined by the response of the first subject given that drug.

If the first subject did not achieve a BIS of 50 or less, then for propofol the dose would be 3 mg/kg and for alphaxalone 0.75 mg/kg.

If the first subject did achieve a BIS of 50 or less, then for propofol the dose would be 1 mg/kg and for alphaxalone 0.25 mg/kg.

Thereafter the dosing is:
a decrease of dose of 25% if all subjects so far treated with that drug achieved a BIS of 50 or,
an increase of dose of 25% if all subjects so far treated with that drug had all not achieved a BIS of 50 or,
In the case that there have been some subjects treated with this drug that have achieved BIS values of 50 or less and others with BIS values that have not fallen to 50 or less then either:
In the case of the last response being a BIS of 50 or less, then the dose of drug for the next subject to receive this drug will be mid way between the dose for the last subject given that drug and the dose given to the most recent previous subject given that drug and who did not achieve a BIS of 50 or below.
In the case of the last response being a BIS greater than 50, then the dose of drug for the next subject to receive this drug will be mid way between the dose for the last subject given that drug and the dose given to the most recent previous subject given that drug who did achieve a BIS of 50 or below.
The latter is repeated for each drug series until the dose range variations have become small and six subjects have achieved a BIS value of 50 or less having received the same dose±10% of drug. These 6 doses achieving anaesthetic levels of BIS are combined to calculate the mean±sem induction dose.

The following results are expected:
Alphaxalone causes general anaesthesia with BIS values <50 achievable in one arm/brain circulation time.
The quality of induction is at least as good as with propofol but with the added advantage of no pain on injection.
At the "induction dose", propofol causes greater falls in blood pressure, an increased incidence of apnoea and decreased oxygen saturation than alphaxalone.
After administration of the "induction dose" the speed and quality of recovery is faster for alphaxalone.
The pharmacokinetics of alphaxalone after intravenous administration are the same as for the alphaxalone figures in the literature after Althesin (Registered Trademark) administration.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of said steps or features.

TABLE 7

Cyclodextrin structures

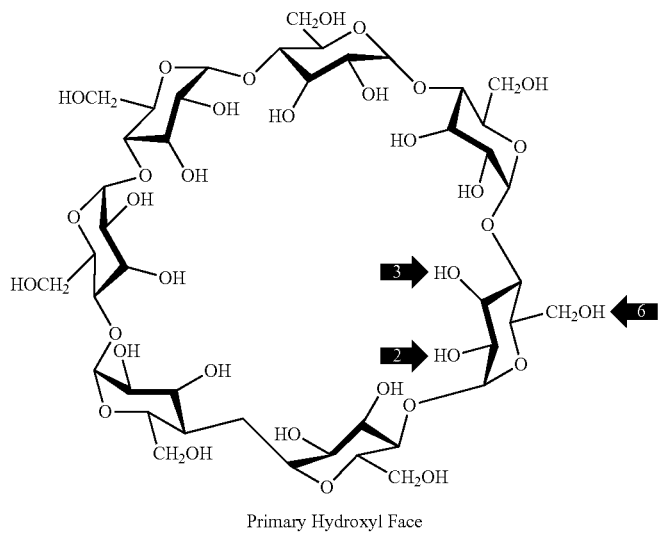

Primary Hydroxyl Face

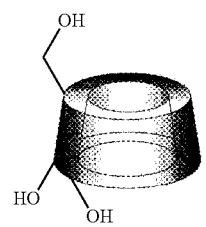

Secondary Hydroxyl Face

TABLE 7-continued

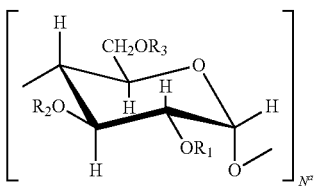

| compd | $R_1$ | $R_2$ | $R_3$ |
|---|---|---|---|
| Hydrophilic Derivatives | | | |
| methylated cyclodextrins | | | |
| 3-mono-O-methylcyclodextrins | H | $CH_3$ | H |
| 2,6-di-O-methylcyclodextrins | $CH_3$ | H | $CH_3$ |
| 2,3,6-tri-O-methylcyclodextrins | $CH_3$ | $CH_3$ | $CH_3$ |
| randomly methylated cyclodextrins | $R_1, R_2, R_3$ = H or $CH_3$ | | |
| hydroxylalkylated cyclodextrins | | | |
| 2-hydroxyethylcyclodextrins | $R_1, R_2, R_3$ = H or $CH_2CH_2OH$ | | |
| 2-hydroxypropylcyclodextrins | $R_1, R_2, R_3$ = H or $CH_2CH(OH)CH_3$ | | |
| 3-hydroxypropylcyclodextrins | $R_1, R_2, R_3$ = H or $CH_2CH_2CH_2OH$ | | |
| 2,3-dihydroxypropylcyclodextrins | $R_1, R_2, R_3$ = H or $CH_2CH(OH)CH_2OH$ | | |
| branched cyclodextrins | | | |
| 6-O-glucosylcyclodextrins | H | H | H or glucose |
| 6-O-maltosylcyclodextrins | H | H | H or maltose |
| 6-O-dimaltosylcyclodextrins | H | H | H or (maltose)$_2$ |
| Hydrophobic Derivatives | | | |
| alkylated cyclodextrins | | | |
| 2,6-di-O-ethylcyclodextrins | $C_2H_5$ | H | $C_2H_5$ |
| 2,3,6-tri-O-methylcyclodextrins | $C_2H_5$ | $C_2H_5$ | $C_2H_5$ |
| acylated cyclodextrins | | | |
| 2,3-di-O-hexanoylcyclodextrins | $COC_5H_{11}$ | $COC_5H_{11}$ | H |
| 2,3,6-tri-O-acetylcyclodextrins | $COCH_3$ | $COCH_3$ | $COCH_3$ |
| 2,3,6-tri-O-propanoylcyclodextrins | $COC_2H_5$ | $COC_2H_5$ | $COC_2H_5$ |
| 2,3,6-tri-O-butanoylcyclodextrins | $COC_3H_7$ | $COC_3H_7$ | $COC_3H_7$ |
| 2,3,6-tri-O-valerylcyclodextrins | $COC_4H_9$ | $COC_4H_9$ | $COC_4H_9$ |
| 2,3,6-tri-O-hexanoylcyclodextrins | $COC_5H_{11}$ | $COC_5H_{11}$ | $COC_5H_{11}$ |
| 2,3,6-tri-O-ocatanoylcyclodextrins | $COC_7H_{15}$ | $COC_7H_{15}$ | $COC_7H_{15}$ |
| Ionizable Derivatives | | | |
| anionic cyclodextrins | | | |
| 6-O-(carboxymethyl)cyclodextrins | H | H | H or $CH_2COONa$ |
| 6-O-(carboxymethyl)-O-ethylcyclodextrins | $C_2H_5$ | $C_2H_5$ | H, $C_2H_5$ or $CH_2COONa$ |
| cyclodextrin sulfate | $R_1, R_2, R_3$ = H or $SO_3Na$ | | |
| sulfobutylcyclodextrins | $R_1, R_2, R_3$ = H or $(CH_2)_4SO_3Na$ | | |

$^a$N = 6, α-CDs; N = 7, β-CDs; N = 8, γ-CDs; N = 9, δ-CDs.

BIBLIOGRAPHY

Atwood, Davies, MacNicol and Vogtie (Eds), *Comprehensive Supramolecular Chemistry* Vol 4, Pergamon: Oxford UK, 1996

Child et al., *British Journal of Anaesthesia* 43:2-13, 1971

Davies and Morris, *Pharmaceutical Research*, 10(7):1093-95, 1993

Fromming and Szejtlic (eds), *Cyclodextrins in Pharmacy*, Kluwer: Dordrecht, The Netherlands, 1994

Remington's Pharmaceutical Sciences, Mack Publishing Company, Eaton, USA, 1990

Rowe's Handbook of Pharmaceutical Excipients, 2009

Thomason, *Crit Rev Ther Drug Carrier Syst* 14:1, 1997

Uekama et al., *Chem. Rev.* 98: 2045-2076, 1998

The invention claimed is:

1. A formulation comprising a neuroactive steroid anaesthetic formulated with a cyclodextrin, wherein the neuroactive steroid anaesthetic is selected from the group consisting of alphadolone, allopregnanolone, ganaxolone, pregnanolone, acebrochol, hydroxydione, minaxolone and tetrahydroxy corticosterone, or a deuterated, tritiated or labelled derivative or salt thereof, and wherein the cyclodextrin is (7) sulfobutyl ether β-cyclodextrin or an alkyl ether derivative thereof and wherein the molar ratio of neuroactive steroid anaesthetic to cyclodextrin is from 1:1.6 to 1:2.5 except for alphadolone where the complexation ratio is from 1:2 to 1:2.5.

2. The formulation of claim 1 wherein the molar ratio of neuroactive steroid anaesthetic to cyclodextrin is from 1:2 to 1:2.5.

3. The formulation of claim 1 further comprising one or more of an antimicrobial agent, a preservative, a buffer and/or a co-polymer.

4. The formulation of claim 3 wherein the formulation comprises a co-polymer selected from the group consisting of hydroxy propyl methyl cellulose, polyvinyl pyrollidone and carboxymethyl cellulose.

5. The formulation of claim 3 wherein the formulation comprises a buffer, and the pH is from about pH 5.5 to about pH 8.

6. The formulation of claim 1 wherein the formulation comprises a derivative, wherein the derivative is sulfobutyl ether-alkyl ether cyclodextrin.

7. The formulation of claim 6 wherein the cyclodextrin is sulfobutyl ether-ethyl ether, β-cyclodextrin or its sodium salt.

8. A method of treating a human subject comprising administering the formulation of claim 1 to said human subject.

9. A method of inducing anaesthesia or sedation in a human subject, said method comprising administering an effective amount of a formulation of claim 1 to said human subject.

* * * * *